United States Patent
Shank et al.

(10) Patent No.: US 6,730,013 B1
(45) Date of Patent: May 4, 2004

(54) METHOD AND APPARATUS FOR LOADING DELIVERY SYSTEMS FOR BRACHYTHERAPY SEEDS

(75) Inventors: Charles E. Shank, Schaunburg, IL (US); John Mueller, Roselle, IL (US); Kevin Helle, Barelett, IL (US)

(73) Assignee: Medi-Physics, Inc., Arlington Heights, IL (US)

( * ) Notice: Subject to any disclaimer, the term of this patent is extended or adjusted under 35 U.S.C. 154(b) by 0 days.

(21) Appl. No.: 09/937,250

(22) PCT Filed: Apr. 7, 2000

(86) PCT No.: PCT/US00/09460

§ 371 (c)(1),
(2), (4) Date: Jan. 3, 2002

(87) PCT Pub. No.: WO00/61229

PCT Pub. Date: Oct. 19, 2000

Related U.S. Application Data

(60) Provisional application No. 60/128,496, filed on Apr. 9, 1999.

(30) Foreign Application Priority Data

May 11, 1999 (GB) ............................................. 9910956

(51) Int. Cl.⁷ ............................ A61N 5/00; A61M 31/00
(52) U.S. Cl. ............................................. 600/7; 604/64
(58) Field of Search .......................... 600/1–8; 221/211, 221/198, 232, 279, 18; 414/146; 250/496.1, 497.1, 507.1; 604/62, 64, 57, 59, 60; 206/535; 482/114, 118; 606/117

(56) References Cited

U.S. PATENT DOCUMENTS

| | | | | |
|---|---|---|---|---|
| 2,620,796 A | * | 12/1952 | Eriksen et al. | 604/62 |
| 4,150,298 A | * | 4/1979 | Brault et al. | 250/497.1 |
| 4,451,254 A | * | 5/1984 | Dinius et al. | 604/62 |
| 4,759,345 A | | 7/1988 | Mistry | |
| 4,891,165 A | | 1/1990 | Suthanthiran | |
| 4,976,686 A | * | 12/1990 | Ball et al. | 604/61 |
| 5,120,973 A | * | 6/1992 | Rohe et al. | 250/497.1 |
| 5,147,282 A | * | 9/1992 | Kan | 600/1 |
| 5,460,592 A | | 10/1995 | Langton et al. | |
| 5,860,909 A | * | 1/1999 | Mick et al. | 600/7 |
| 5,906,574 A | * | 5/1999 | Kan | 600/7 |
| 6,048,300 A | * | 4/2000 | Thornton et al. | 600/7 |
| 6,102,844 A | * | 8/2000 | Ravins et al. | 600/8 |
| 6,106,455 A | * | 8/2000 | Kan | 600/7 |
| 6,113,529 A | * | 9/2000 | Shi | 600/7 |
| 6,196,953 B1 | * | 3/2001 | Buchanan | 482/114 |
| 6,213,932 B1 | * | 4/2001 | Schmidt | 600/7 |
| 6,428,463 B1 | * | 8/2002 | Ravins et al. | 600/7 |

FOREIGN PATENT DOCUMENTS

| | | |
|---|---|---|
| DE | 10 95 963 B | 12/1960 |
| EP | 0 466 681 A1 | 7/1991 |
| FR | 2 287 894 A | 5/1976 |
| GB | 1 308 041 A | 2/1973 |
| WO | WO 97/22379 A | 6/1997 |

* cited by examiner

*Primary Examiner*—Eric F. Winakur
*Assistant Examiner*—Nikita Veniaminov
(74) *Attorney, Agent, or Firm*—Robert F. Chisholm; Li Cai

(57) ABSTRACT

The present invention provides apparatus and methods for loading delivery systems, such as seed magazines and suture material, with seeds which greatly increases productivity, reduces process variation and reduces the risk of handling damage to the seeds. Importantly, the apparatus and methods of the present invention reduce potential risks to workers. In a first aspect of the invention there is provided an automated method of loading a delivery system for brachytherapy seeds which comprises the steps of a) securing the delivery system to be loaded; b) conmnunicating seeds from a supply of seeds into the delivery system; and c) repeating step b) to load a plurality of seeds. In a second aspect of the invention there is provided an apparatus for loading a delivery system for brachytherapy seeds comprising: a) means for retaining a delivery system to be loaded with seeds; and b) means for communicating individual seeds from a supply of seeds to said delivery system.

33 Claims, 20 Drawing Sheets

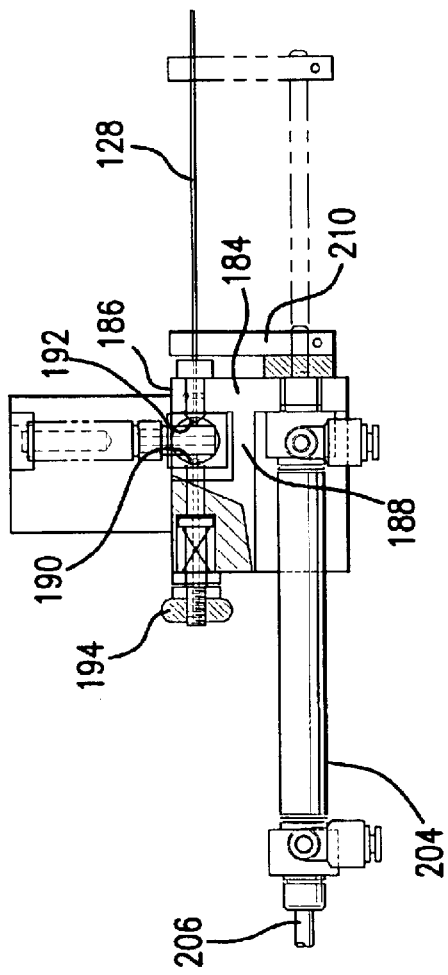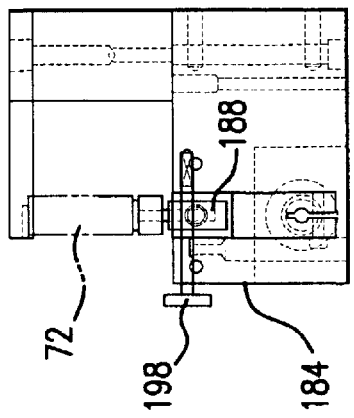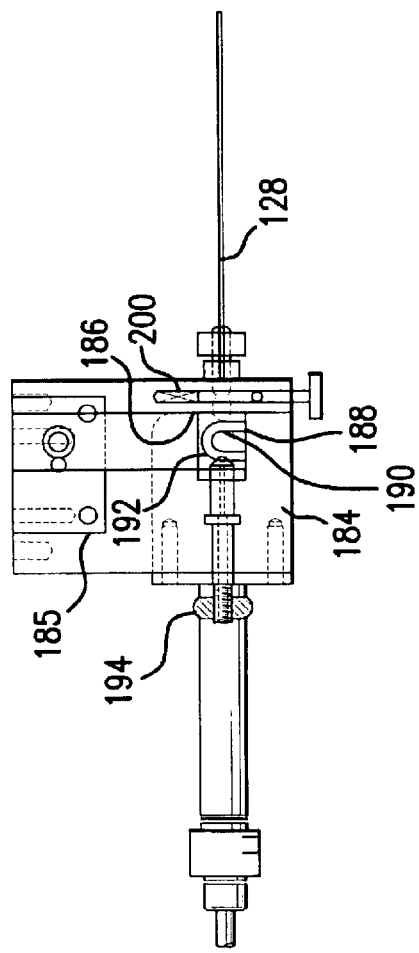

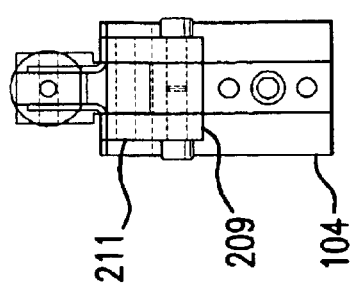
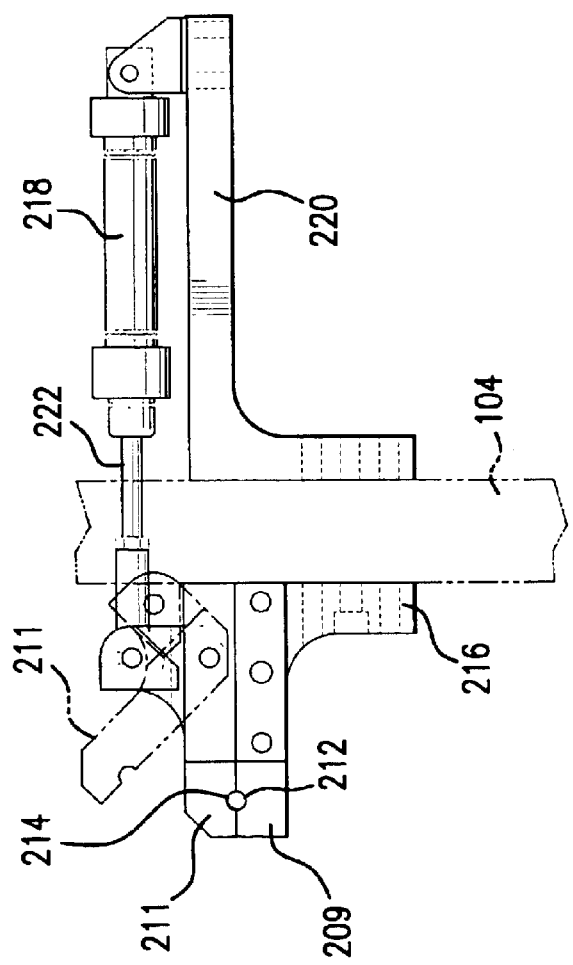
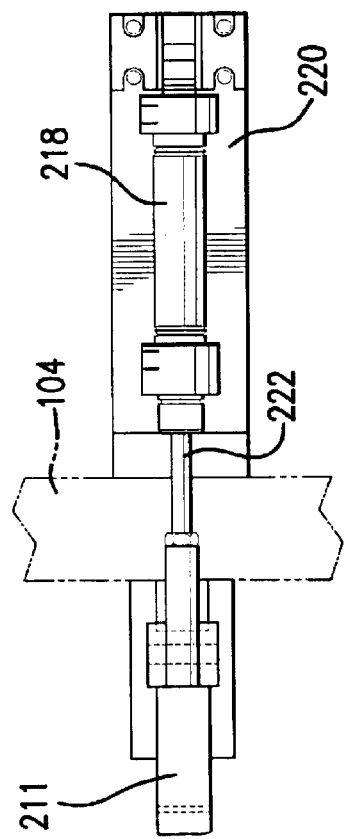
FIG. 34
FIG. 32
FIG. 33

METHOD AND APPARATUS FOR LOADING DELIVERY SYSTEMS FOR BRACHYTHERAPY SEEDS

This application claims the benefit of Provisional application Ser. No. 60/128,496, filed Apr. 9, 1999.

BACKGROUND OF THE INVENTION

1. Field of the Invention

The present invention relates generally to brachytherapy seeds used for radiation therapy. More particularly, the present invention relates to methods and apparatus for loading delivery systems for brachytherapy seeds used in radiation therapy.

2. Description of the Related Art

Radiation therapy is the treatment of diseases, especially the treatment of tumors, including malignant tumors, with radiation. In radiation therapy, the ultimate aim is to destroy the malignant tissue without causing excessive radiation damage to nearby healthy, and possibly vital, tissue. This is difficult to accomplish because of the proximity of malignant tissue to healthy tissue.

Medical personnel and investigators have developed methods for preferentially irradiating deep seated diseased tissue as opposed to healthy tissue. These methods include the use of high energy x-ray beams together with cross fire and rotational techniques which create a radiation pattern that is maximized at the site of the diseased tissue. Nonetheless, some absorption and damage inevitably occurs to healthy tissue in the path through which radiation passes to arrive at deep seated diseased tissue.

One method of limiting the zone of irradiation utilizes radioactive "seeds," which are permanently implanted at the zone to be irradiated. Such seeds contain a radioactive isotope disposed within a capsule. The seeds are injected or implanted into body tissue at the site to be treated. The small size of therapeutic seeds allows the seeds to be inserted within tissue to be treated, in order to totally surround the tissue.

The advantage of interstitial implantation of a radiation-emitting article for localized tumor treatment have long been recognized. Interstitially implanted articles concentrate the radiation at a zone where radiation treatment is needed, i.e., near or within the tumor in order to directly affect surrounding tumor tissue, while exposing normal, healthy tissue to substantially less radiation than beaming radiation into the body from an external source.

Implanting radioactive articles directly into solid tumors to destroy the tumors is a therapy referred to as brachytherapy (i.e., short-range therapy). This form of therapy permits the application of larger doses of radiation directly to the tumor.

A seed applicator, such as shown and described in U.S. Pat. Nos. 5,860,909 and 5,242,373, the disclosures of which are hereby expressly incorporated herein by reference, can be used to accomplish correct placement of the seeds. The apparatus described in these patents are operable to implant individual seeds in spaced relationship.

Another method and approach for implanting brachytherapy seeds in or near a tumor utilizes seeds loaded within suture material, such as the RAPID STRAND® product available from Medi-Physics, Inc. Also, see Langton, et. al. U.S. Pat. No. 5,460,592, the disclosure of which is hereby incorporated herein by reference. The seeds are precisely positioned within the suture material, which may then be stiffened to retain the seeds therein and in their precise locations. An introducer is used to implant the strand of seed containing suture within the patient. The suture material retains the seeds at the desired locations until healing incorporates them into the tissue. The suture material is also bioabsorbable, and upon biodegradation of the suture material, the seeds are held in the tissue at the desired locations and with precise spacing.

The seeds utilized in either of these applications are remarkably small. The radioactive material itself, usually a portion of doped wire, is inserted and retained within a capsule. The capsule is typically a cylinder of less than 0.1550 in length and less than 0.030 in diameter. Alternatively, the capsule may have a spherical or oval shape To facilitate handling of the seeds during implantation, the applicators described in U.S. Pat. Nos. 5,860,909 and 5,242,373 utilize a magazine that holds a number of seeds. The seeds are delivered from the magazine into the applicator, from which they are implanted within the patient. The RAPID STRAND® product itself retains the seeds and facilitates handling during implantation.

While use of applicators or the RAPID STRAND® product greatly facilitates the implantation of seeds into patients, the loading of seeds into magazines or suture material remains largely a manual task. A worker given sufficient training and learning time can become quite skilled at the tasks necessary for loading a magazine or suture with seeds. At best, however, the worker may become capable of preparing a single magazine or strand of suture in several minutes time. In addition, aside from the labor intensive nature of this process, fatigue, repetitive motion injuries and radiation exposure limit the time a skilled worker may continue in the task. Manual magazine or suture loading also requires the use of tweezers, necessary for handling the small seeds, which may also result in damage to the seeds, and process variation remains worker dependant and difficult to control.

SUMMARY OF THE INVENTION

The present invention provides apparatus and methods for loading delivery systems, such as seed magazines and suture material, with seeds which greatly increases productivity, reduces process variation and reduces the risk of handling damage to the seeds. Importantly, the apparatus and methods of the present invention reduce potential risks to workers.

In a first aspect of the invention there is provided an automated method of loading a delivery system for brachytherapy seeds which comprises the steps of:

a) securing the delivery system to be loaded;

b) communicating seeds from a supply of seeds into the delivery system; and c) repeating step b) to load a plurality of seeds.

In a second aspect of the invention there is provided an apparatus for loading a delivery system for brachytherapy seeds comprising:

a) means for retaining a delivery system to be loaded with seeds; and b) means for communicating individual seeds from a supply of seeds to said delivery system.

In one embodiment of either the first or second aspect of the present invention, a magazine to be loaded with seeds is positioned within a loading fixture. A vibratory feeder communicates seeds to a staging area adjacent the fixtured magazine, and a pusher member cycles to load seeds from the staging area into the magazine.

In another embodiment of either the first or second aspect of the present invention, suture material is loaded onto a cannula, which is then precisely positioned within the loading apparatus. A magazine containing a plurality of seeds is loaded to the loading apparatus. Seeds are introduced from the magazine into the cannula, and a pusher communicates the seeds along the cannula and proximate to an end thereof. A gripper, positioned adjacent the end of the cannula retracts the suture material drawing the seed from the cannula along with a precise length of suture material. The loader apparatus is operated until a desired number of seeds are loaded within the suture material, which is then removed from the loader and arranged for subsequent finish processing.

Definitions:

The following are definitions of various terms used in the foregoing specification.

Brachytherapy seed: A brachytherapy seed comprises: (1) a radioactive source, comprising (a) a radioisotope, disposed on (b) a carrier, and (2) a casing containing the radioactive source. In some embodiments, the carrier also serves as the casing.

The seed is of an overall size and dimensions suitable for its intended use. Seeds for use in the treatment of prostate cancer are, for example, typically substantially cylindrical in shape, about 4.5 mm long with a diameter of 0.8 mm. For use in the treatment of restenosis, a seed is of suitable dimensions to be inserted inside a coronary artery, for example, a length of about 10 mm and a diameter of about 1 mm, preferably a length of about 5 mm and a diameter of about 0.8 mm, and most preferably a length of about 3 mm and a diameter of about 0.6 mm. A seed also can be oval or substantially spherical in shape.

Radioisotope: The radioactive isotope disposed on the surface of the carrier is not limited and is selected based on the type and strength of the radiation that is desired, the half-life of the radioisotope, and the disease or condition to be treated. Non-limiting examples of useful radioisotopes include iodine-125, palladium-103, cesium-131, gold-198, thulium-170, chromium-56, arsenic-73, yttrium-90, and mixtures thereof. In addition, radioactive isotopes of samarium, tantalum, radon, radium, cobalt, iridium, and mixtures thereof, also can be used in brachytherapy seeds. Other gamma ray emitting elements and radioactive isotopes, including mixtures of one or more radiation sources capable of emitting therapeutically useful forms of radiation (e.g., gamma rays, alpha particles, beta particles, Auger electrons, X-rays, and electromagnetic waves) also are useful, provided they are presented in a form and in amounts which are useful in radiation therapy. Several other examples of useful radioisotopes are disclosed in Good, U.S. Pat. No. 5,342,283, the disclosure of which is hereby expressly incorporated herein by reference. The radioactive isotope is applied to the carrier by techniques that are well known in the art. Particularly preferred radioisotopes included palladium-103 and iodine-125.

Carrier: Suitable carriers for the radioisotopes include, but are not limited to, support materials, such as plastics, graphite, zeolites, ceramics, glasses, metals, polymer matrices, ion-exchange resins, and other, preferably porous, materials. The support material can be in the form of a bead, wire, or rod. The support materials can be encapsulated in a hollow sealed casing, for example a metal container, or the support material can be coated with an electroplated shell, for example a layer of a metal, such as silver or nickel. Alternatively, the carrier can be a hollow sealed container directly encapsulating the radioisotope, without, for example, the need for a biocompatible support material.

The carrier incorporating the radioisotope also can be a polymer matrix, or a plastic or ceramic composite, and/or may form part of a container wall. For example, if a metal alloy is used to form a container, then a component of the alloy can be a suitable radioisotope. If a container is made from a composite material, a component of the composite may be a suitable radioisotope.

Specific, non-limiting, examples of carriers are silver and copper because these metals provide good X-ray visualization and because commonly used radioactive isotopes, such as iodine and palladium, can be easily attached to a silver or copper surface by chemical or electroplating processes. Other X-ray opaque metals, such as gold and iron, for example, can be used as a carrier for purposes of the invention. Likewise, a suitable metal can be deposited (chemically or by using "sputtering" and "ion plating" techniques) onto a substrate other than a metal, e.g., a polypropylene filament, preferably such that the thickness of the metallic coating on the substrate exceeds about 0.050 mm to ensure X-ray visualization.

Casing: Suitable casing materials include biocompatible metals or metal alloys such as titanium, gold, platinum and stainless steel: plastics such as polyesters and vinyl polymers of polyurethane, polyethylene and poly(vinyl acetate); composites of graphite, and glass such as matrices comprising silicon oxide. The container also can be plated on the outside with a biocompatible metal, for example, gold or platinum.

Preferred suitable casing materials are biocompatible metals, and typically low atomic numbered metals, such as stainless steel alloy or titanium. Higher atomic number metals, such as gold and platinum, attenuate too much radiation emanating from the radioisotope-laden carrier to be useful per se. However, higher atomic numbered biocompatible metals are useful as a plating over various low atomic number materials such as beryllium, which otherwise is too toxic if used without an outer coating. Other suitable casing materials include, but are not limited to, tantalum, nickel alloys, copper alloys, and aluminum alloys.

Titanium, which has a low atomic number and a high strength-to-weight ratio, is the most preferred casing material. Titanium is exceptionally corrosion-resistant, and is satisfactory from the standpoint of tissue compatibility and non-toxicity. Preferably, the titanium is a pure alloy to assure good working properties.

The casing can have at least part of one surface of which is roughened, shaped, or otherwise treated whereby ultrasound visibility of the seed is enhanced.

Suture Material: The suture material is a bioabsorbable material made of any natural or synthetic material that is absorbable in a living body. Non-limiting examples of natural absorbable materials, as disclosed in U.S. Pat. No. 4,697,575, are the polyester amides from glycolic or lactic acid, such as the polymers and copolymers of glycolate and lactate, polydioxanone and the like. Such polymeric materials are more fully described in U.S. Pat. Nos. 3,565,869; 3,636,956; 4,052,988 and European Patent Application 30822. Specific and non-limiting examples of absorbable polymeric materials that can be used as suture materials are polymers marketed by Ethicon, Inc., Somerville, N.J. under the trademarks "VICRYL" and "PDS."

The suture material preferably maintains its integrity for from 1 to about 14 days. Preferably, the suture material is absorbed in living tissue in a period of time from about 70–120 days.

BRIEF DESCRIPTION OF THE DRAWINGS

FIG. 23 is a partial front elevation of the apparatus illustrated in FIG. 10;

FIG. 24 is a plan view of the portion of the apparatus illustrated in FIG. 23;

FIG. 25 is a side elevation of the portion of the apparatus illustrated in FIG. 23;

FIG. 32 is a partial front elevation view of a portion of the apparatus illustrated in FIG. 10;

FIG. 33 is a partial plan view of the portion of the apparatus illustrated in FIG. 32;

FIG. 34 is a partial left side elevation of the portion of the apparatus illustrated in FIG. 32;

DETAILED DESCRIPTION OF THE PREFERRED EMBODIMENTS

Figure 1:
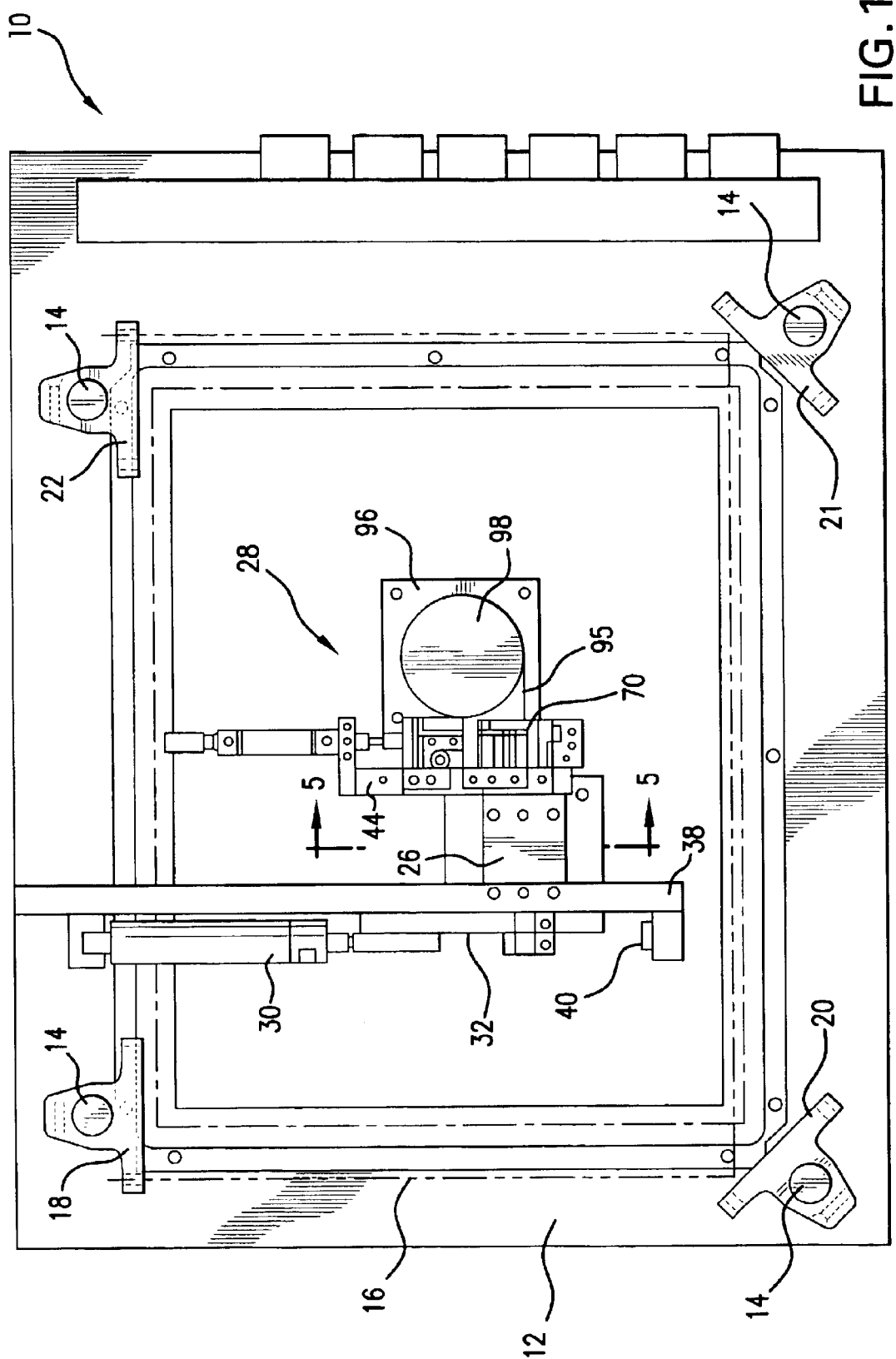
FIG. 1 is a front elevation view of an apparatus in accordance with a preferred embodiment of the present invention.

The invention is described as follows in terms of several preferred embodiments. These embodiments should be taken only as examples of preferred implementations, and in no way should be considered limiting of the invention.

Referring to the drawings, FIGS. 1–9 illustrate a magazine loading apparatus 10 supported on a base 12. Secured to the base 12 are a plurality of standards 14 supporting elements of a safety light curtain (illustrated in phantom as 16). A light emitter 18 sends a light beam that is reflected by a first mirror element 20 and a second mirror element 21 to a light receiver 22. The light curtain 16 operates as is well known for inhibiting operation of apparatus 10 when a portion of an operator's body or any other object is located in a manner that may interfere with operation of the apparatus 10.

Figure 2:
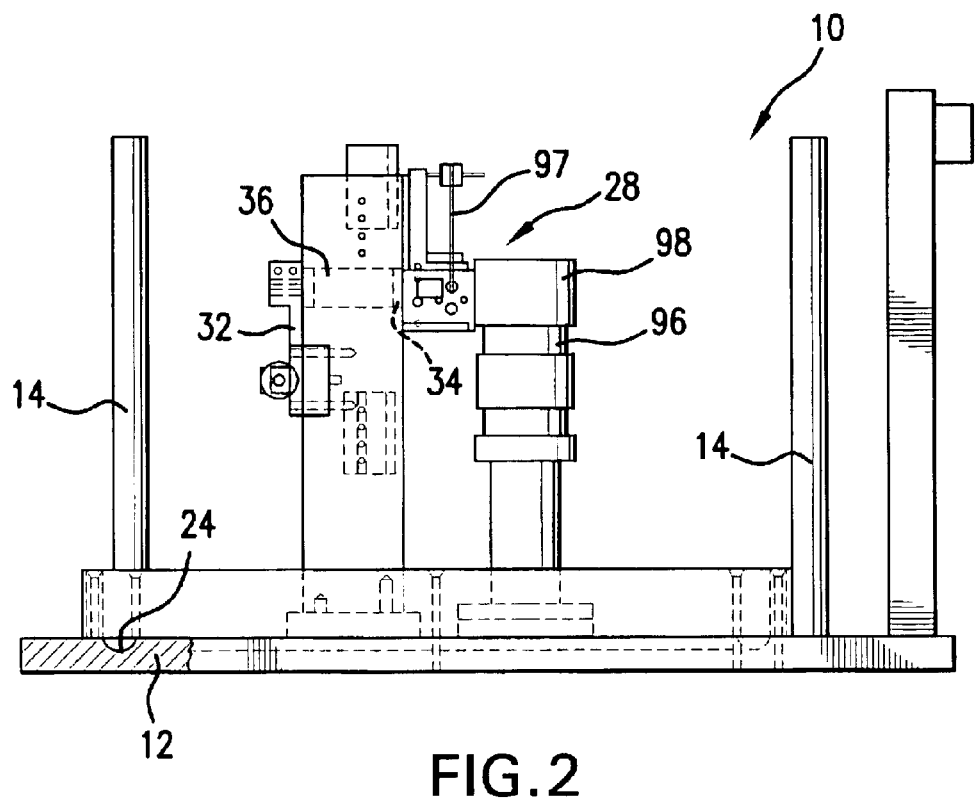
FIG. 2 is a plan view of the apparatus shown in FIG. 1.
Figure 3:
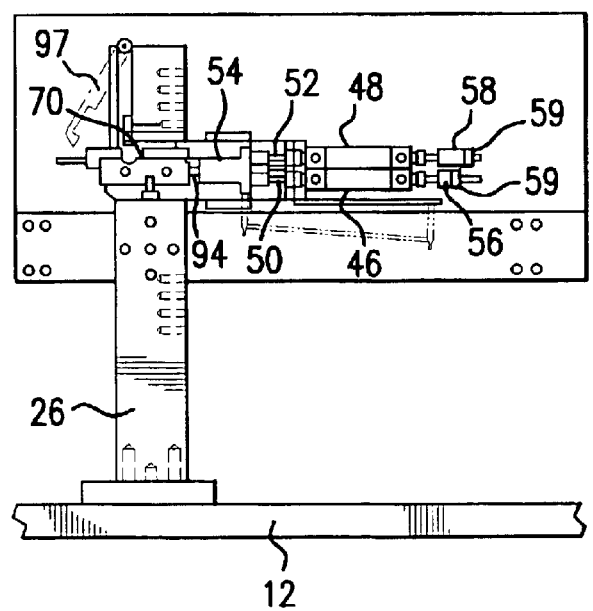
FIG. 3 is aright side elevation of the apparatus shown in FIG. 1.
Figure 4:
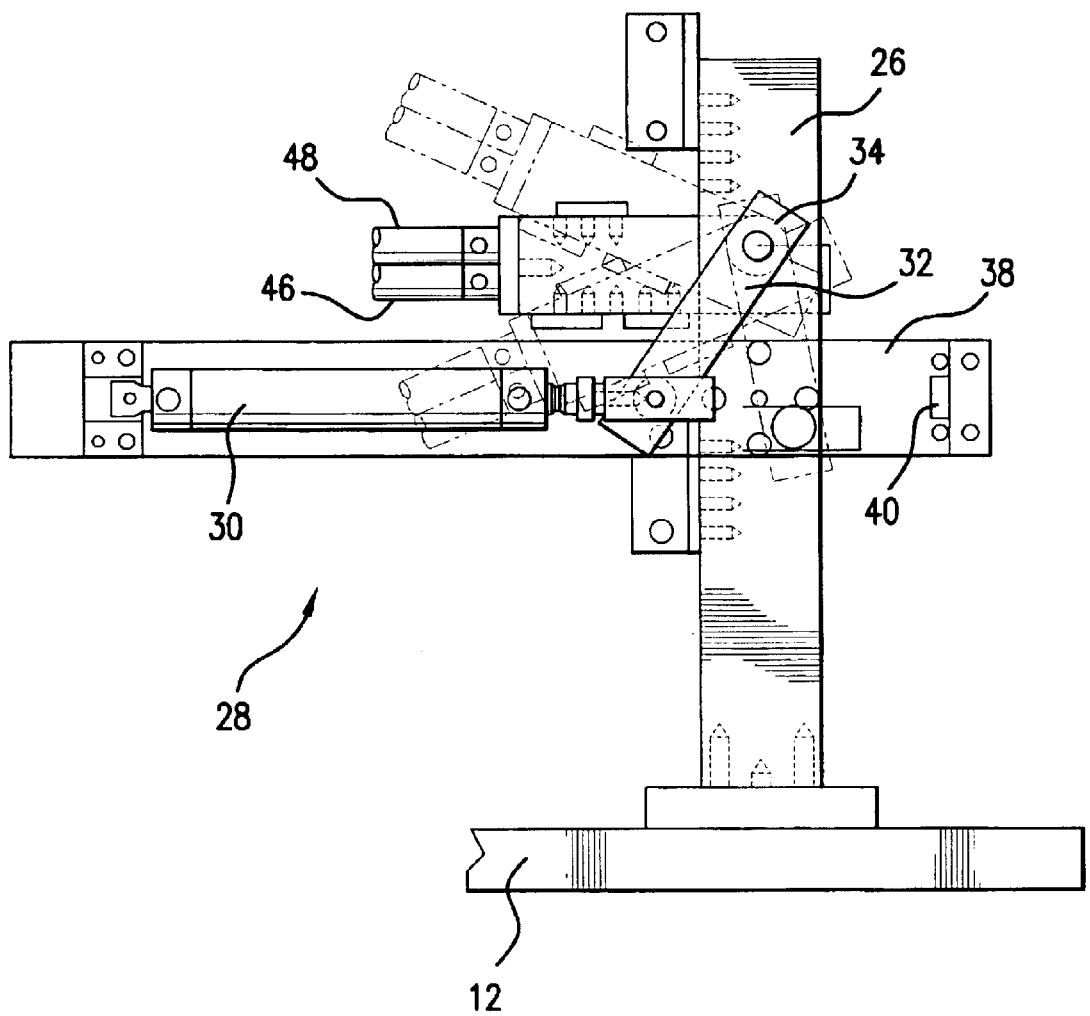
FIG. 4 is a left side elevation of the apparatus shown in FIG. 1.
Figure 5:
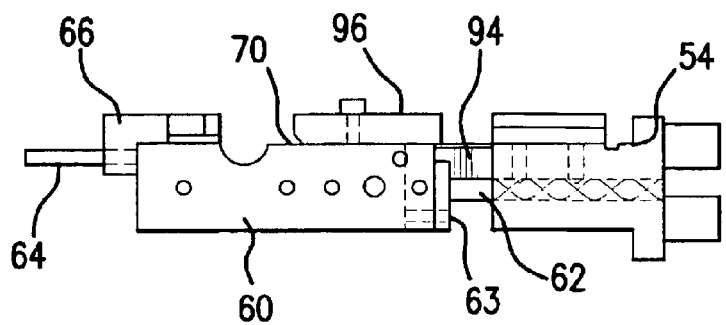
FIG. 5 is a partial cross-section view taken along line 5—5 of FIG. 1.
Figure 6:
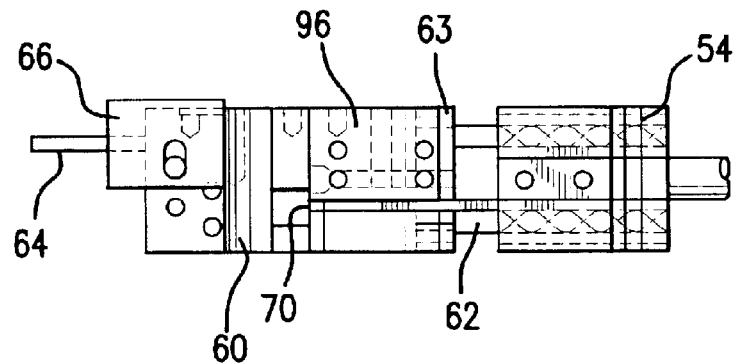
FIG. 6 is a partial plan view of the portion of the apparatus illustrated in FIG. 5.

As shown in FIG. 2, base 12 is formed from a plate, preferably metallic and, more preferably, aluminum, and includes a channel 24 extending about a periphery thereof As will be appreciated from the following discussion, channel 24 advantageously captures seeds which may be inadvertently ejected from the apparatus 10. Furthermore, base 12 is preferably painted or anodized a color that contrasts with the color of the seeds to make locating them should they fall onto base 12 and into channel 24 easier.

A vertical support 26 extends from the base 12 and pivotably secured thereto is a magazine loader 28. More particularly, an air cylinder 30 couples to an arm 32 that is coupled to a pivot shaft 34 journally supported on a sleeve bearing 36 through the vertical support 26. A bracket 38 is secured to the vertical support 26 and includes a bumper 40 for the arm 32. The air cylinder 30 is operable to pivot the magazine loader 28 between a first position and a second position. Pivoting the magazine loader 28 facilitates insertion of a magazine 72 therein, provides for orderly insertion of seeds 99 into magazine 72, and advantageously utilizes the shielding properties of the stainless steel to reduce the radiation exposure to the operator.

Supported on the pivot shaft 34 is a right-angled swing arm 44 onto which are secured a first air cylinder 46 and a second air cylinder 48. Each include a drive rod, 50 and 52 respectively, that couple at a first end to a slide block 54. Disposed opposite slide block 54, each drive rod, 50 and 52, includes a bumper stop 56 and 58, respectively, secured by a clamp 59. The bumper stops 56 and 58 are sized to provide a first stroke length and a second stoke length, respectively.

A tooling nest 60 is secured to the swing arm 44 and a slide rod 62 extends outwardly therefrom and is secured thereto by a block 63. The tooling nest is preferably constructed from a radiation shielding material. The slide block 54 slides on the slide rod 62 and with respect to the tooling nest 60 responsive to driving action of either first air cylinder 46 or second air cylinder 48. Further extending from the tooling nest 60 is a dowel 64 onto which a hold down block 66 slides. Hold down block 66 is further biased in a first position by action of a bias spring (not shown).

The tooling nest 60 is formed with a receiver area 70 adapted to receive the magazine 72, which is preferably constructed in accordance with the aforementioned U.S. Pat. Nos. 5,860,909 and 5,242,373. Once positioned within receiver area 70, a loading end 74 of the magazine 72 is positioned adjacent a staging area 76.

Figure 7:
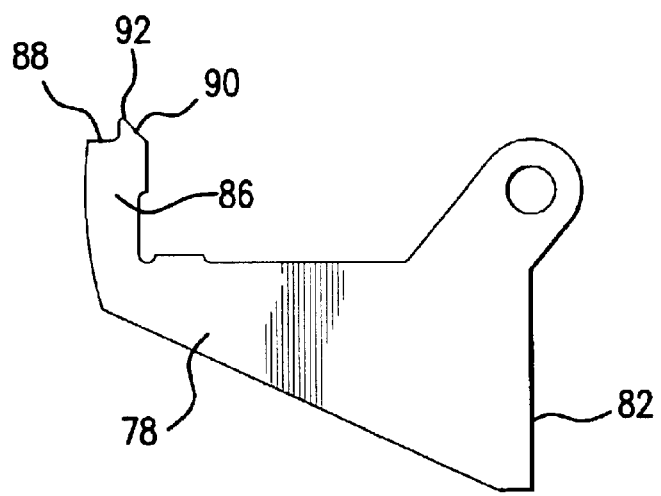
FIG. 7 is a front elevation view of a seed loading finger in accordance with the preferred embodiments of the present invention.
Figure 8:
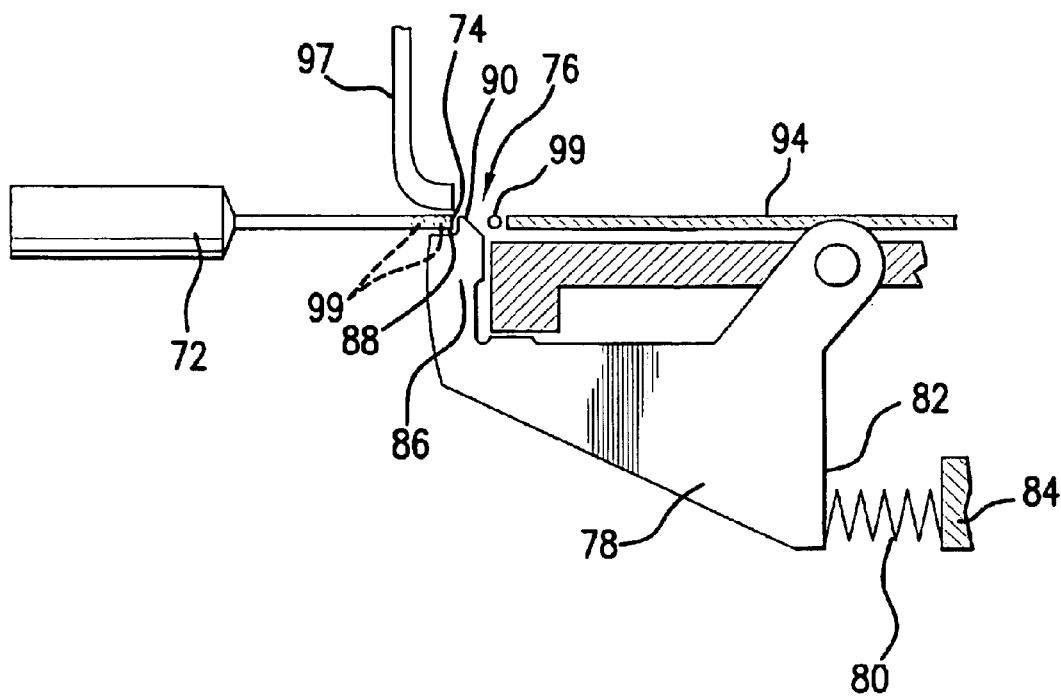
FIG. 8 is a partial cross-section view taken along line 8—8 of FIG. 6 illustrating the apparatus in a first operating position.
Figure 9:
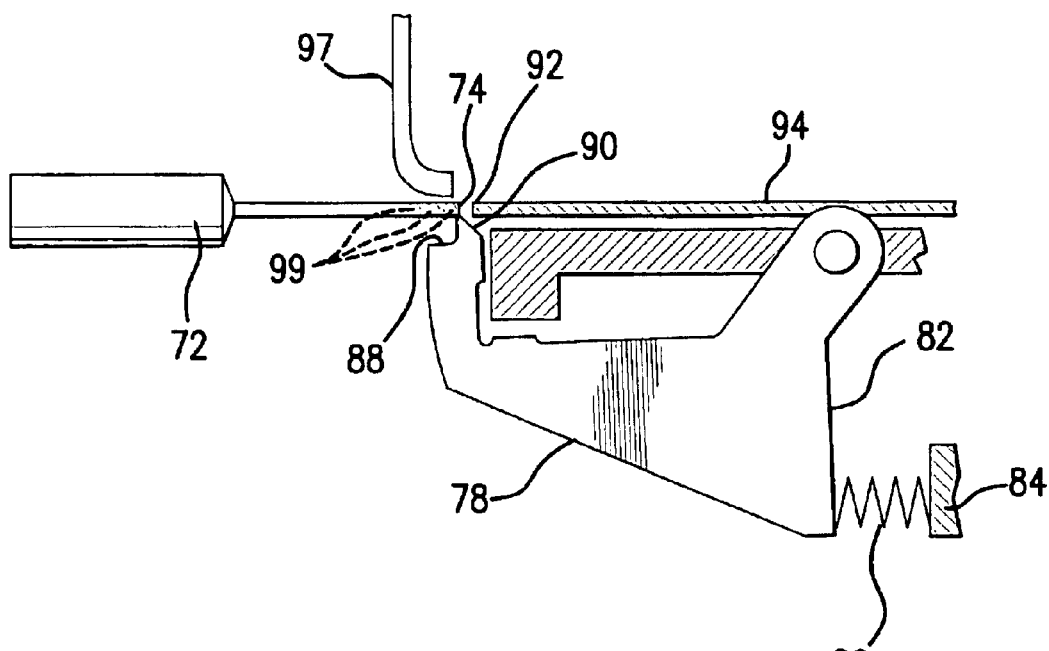
FIG. 9 is a view similar to FIG. 8 illustrating the apparatus in a second operating position.
Figure 10:
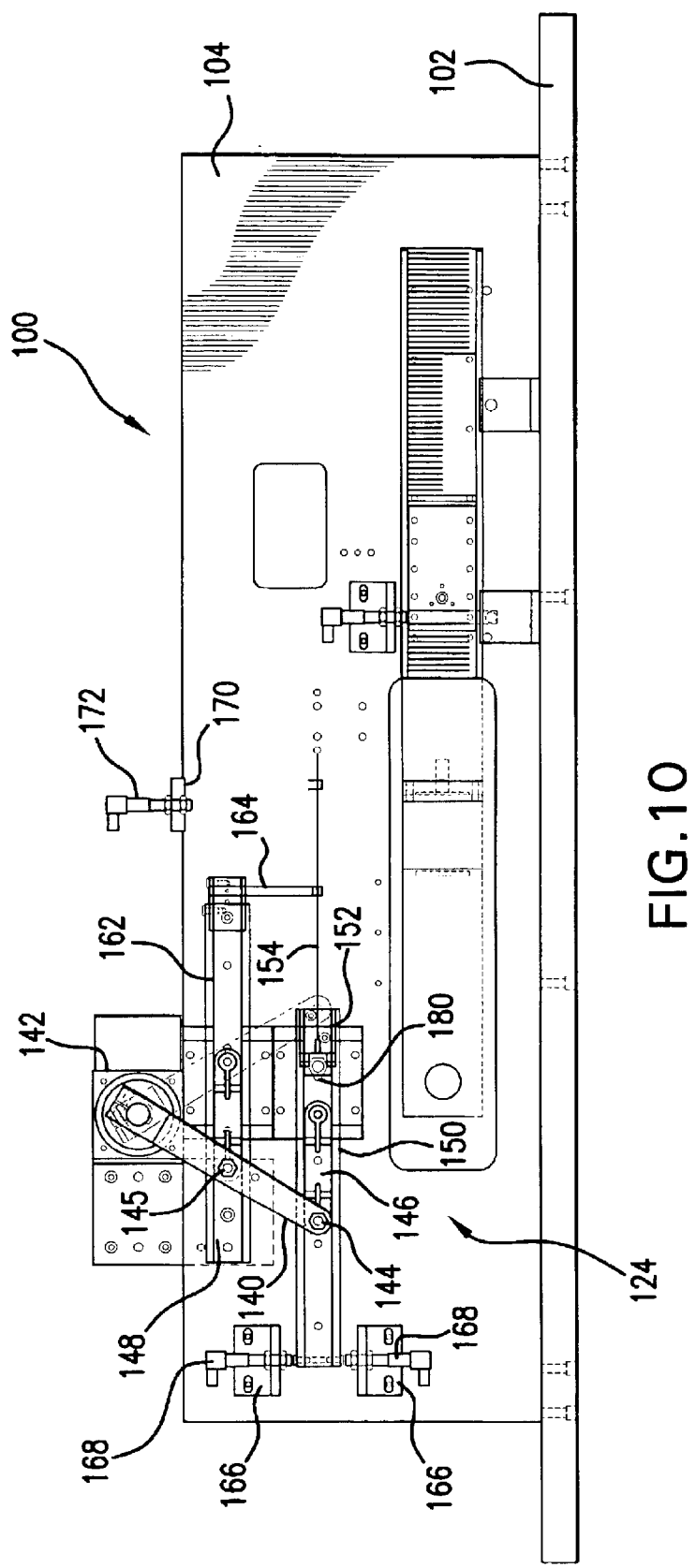
FIG. 10 is a front elevation view of an apparatus in accordance with an second preferred embodiment of the present invention.
Figure 11:
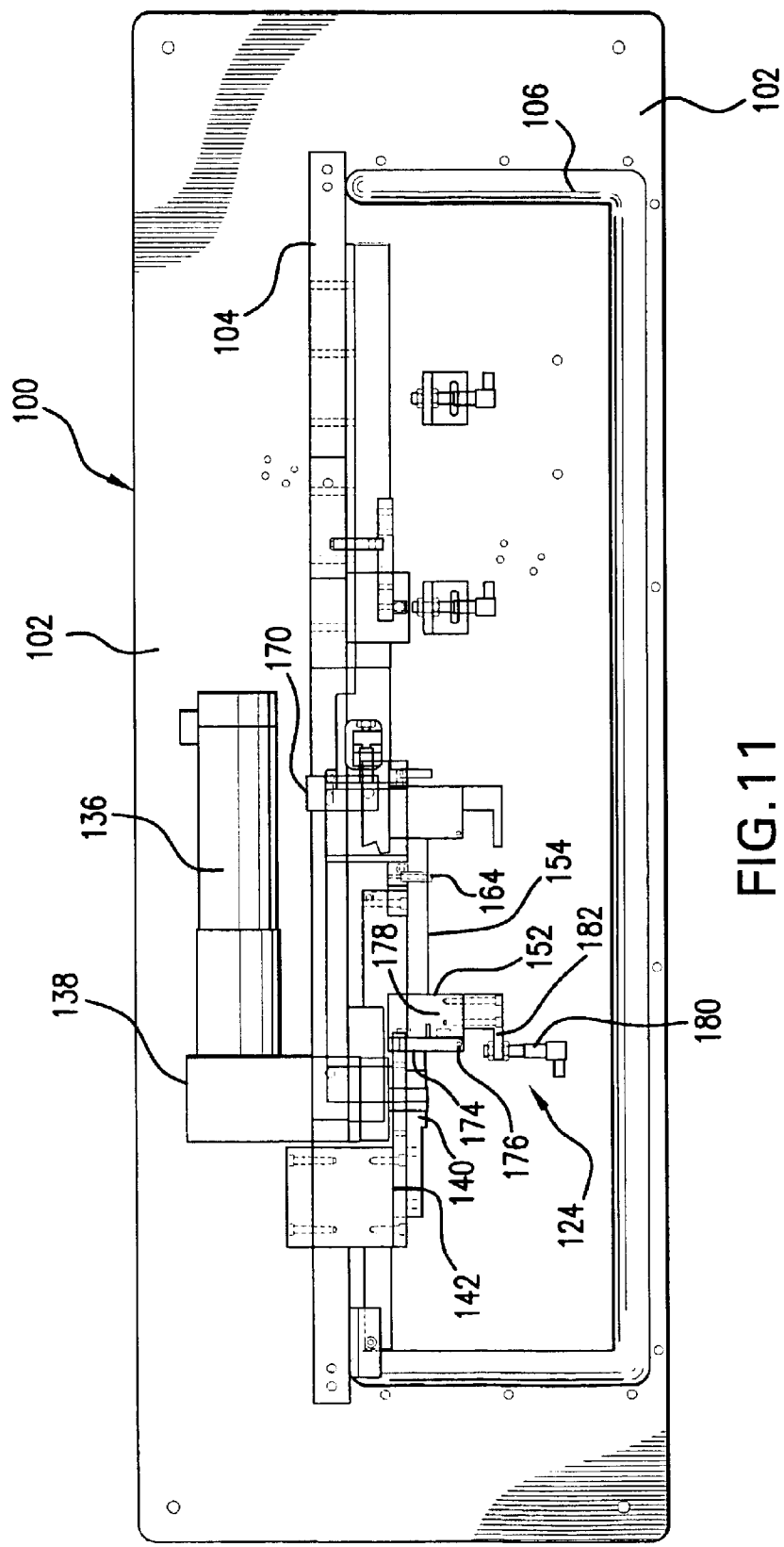
FIG. 11 is a plan view of the apparatus show in FIG. 10.

Pivotably secured to an underside portion of tooling nest 60 is a finger member 78 (best seen in FIGS. 7–9). The finger member 78 is biased in a first position by a spring 80 which bears between a lower portion 82 of the finger member 78 and an end block 84 of the tooling nest 60. An upper portion 86 of the finger member 78 is formed with a notch portion 88 and an angled portion 90 forming a finger 92.

Secured to the slide block 54 is a pusher member 94. The pusher member 94 has a rectangular shape including a width approximately the length of a seed and a thickness approximately the diameter of a seed. The pusher member 94 slides relative to the receiver area 70. A clear cover 96 is secured to an upper portion of the tooling nest 60 and adjacent to the receiver area 70.

Further secured to the base 12 is a vibratory feeder 96 including a hopper 98 and a feed path 95 leading from the hopper 98 to the receiver area 70. The vibratory feeder 96 is sized and its operating frequency is, preferably, tuned such that approximately 1500–2500 seeds may be loaded therein and such that hopper 98 substantially completely empties between batches. The vibratory feeder 96 is adapted to align seeds end-to-end along the feed path 95 and to communicate the seeds from the hopper 98 to the staging area 76. An air jet (illustrated in the attached photographs) is further coupled adjacent feed path 95 to assist seeds communicated along feed path 95 toward the staging area 76 and to ensure all seeds are emptied from the hopper 98.

The entire apparatus 10 is secured within a housing (not shown) which includes radiation shielding and access hatches as is very well known in the art. Preferably operation of apparatus 10 may be viewed through a lead loaded acrylic viewing window formed in the housing, and access to the apparatus during operation is by access gloves.

The seed loading process begins with the swing arm 44 in the first position in which the tooling nest 60 is preferably tilted down and forward to allow access thereto. A magazine 72 is inserted into the receiver area 60 with the loading end 74 adjacent the staging area 76. Air cylinder 46 is actuated to move pusher member 94 to its fully extended position, and the loading end 74 of the magazine 72 is secured over pusher member 94. Actuation of the air cylinder 30 then pivots magazine loader 28 to the second position.

Referring to FIGS. 8 and 9, in the second position, staging area 76 is adjacent the feed path 95. The air cylinder 46 is retracted, which permits the finger member 78 to move to its first position, and to introduce a seed 99 communicated along feed path 95 into staging area 76. Repeated actuation of air cylinder 98 then acts to load a plurality of seeds 99 into the magazine 72. Forward motion of pusher member 94 engages the seed 99 and the angled surface 90 of the finger member 78 causes it to move it to its second position. Further forward motion of the pusher member 94 then introduces the seed into the loading end 74 of the magazine 72. As the pusher member 94 is retracted, the finger member 78 then moves again to its first position to retain the loaded seed 99 within the magazine and to allow a next seed 99 into the staging area 76. To load the final seed 99 into the magazine 72, air cylinder 46 is actuated which introduces the final seed 99 into the magazine 72 and further advances pusher member 94 to its fully extended position to secure and retain the seeds 99 within the magazine 72. A swing arm 97 is provided pivoted from vertical support 26. With the magazine loader 28 in the second position, swing arm 97 is disposed over staging area 76 to assist in directing the seeds 99 into the magazine 72 and for retaining the seeds 99 therein. The components shown in FIGS. 8 & 9 are, preferably, constructed from stainless steel in order to be resistant to rusting.

Air cylinder 30 is then actuated to pivot magazine loader 28 back to its first position so that the now loaded magazine 72 may be removed from the apparatus 10. Cycle time is approximately about 7.5 seconds as compared to minutes for manual loading. Furthermore, the process significantly reduces operator repetitive motions, fatigue and radiation exposure.

FIGS. 10–37 illustrate an apparatus 100 for loading seeds into suture material 101. Apparatus 100 includes a base 102 and a wall 104 extending substantially perpendicularly from base 102. Base 102 is formed with a channel 106 and has secured thereto side shields, 108–112, respectively (best seen in FIG. 16). Base 102 and wall 104 are preferably made of painted or anodized aluminum to contrast the color of the seeds. Side shields 108–112 and channel 106 cooperate to contain seeds that may be inadvertently ejected from the apparatus 100 during loading. A plurality of standards 114 extend from base 102 and support elements of a safety light curtain (shown in phantom as 116). A light emitter 18 sends a beam of light to a light receiver 122. The light curtain 116 is coupled to a control system for apparatus 100 and operates as is well known for inhibiting operation of the apparatus 100 when a portion of an operator's body or any other object is located in a manner that may interfere with operation of the apparatus 100.

Figure 14:
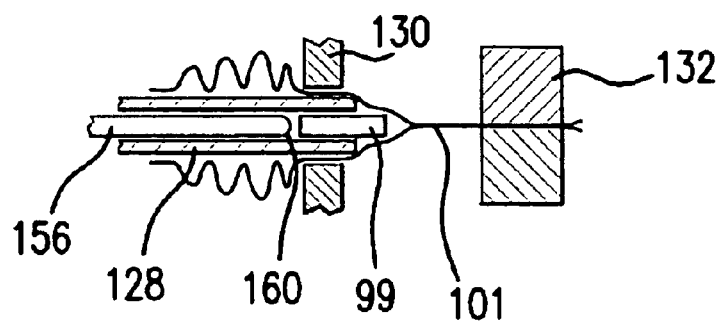
FIG. 14 is a schematic illustration of a first operating position of the apparatus shown in FIG. 10.
Figure 15:
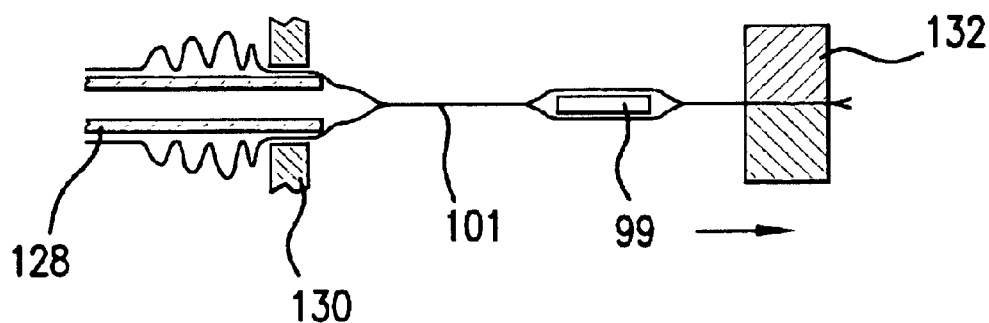
FIG. 15 is a view similar to FIG. 14 illustrating a second operating position of the apparatus shown in FIG. 10.
Figure 15A:
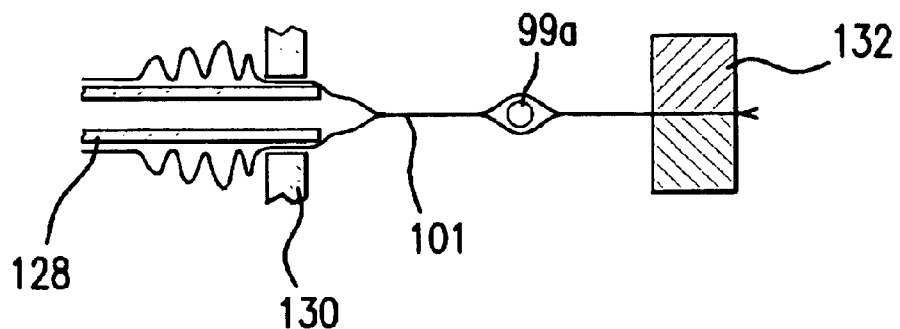
FIG. 15a is a view similar to FIG. 15 illustrating insertion of spherical seeds into suture material.
Figure 16:
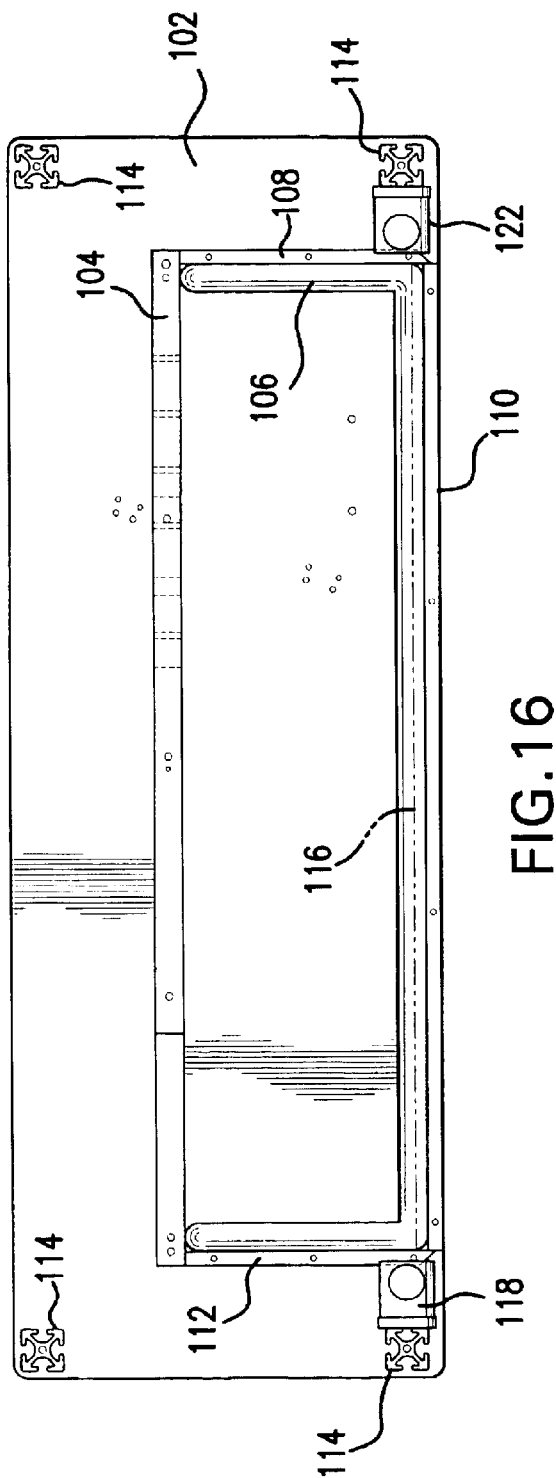
FIG. 16 is a partial plan view of the apparatus illustrated in FIG. 10.
Figure 17:
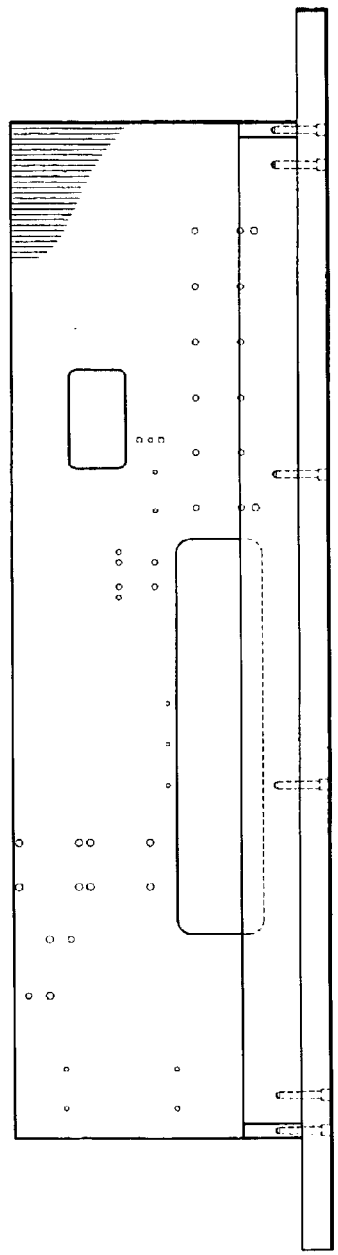
FIG. 17 is a partial front elevation of the apparatus illustrated in FIG. 10.

Referring still to FIGS. 10–13 and now more particularly to FIGS. 14 and 15, apparatus 100 includes a seed pusher portion 124 and a suture feeder portion 126. In general, seed pusher portion 124 is adapted to accept a seed 99 from a magazine. The magazine may be any suitable magazine holding a plurality of seeds. Preferably, the magazine is a magazine 72 as described above and loaded with seeds 99 using apparatus 10. The magazine permits introduction of a plurality of seeds 99 into a cannula 128. The pusher portion 124 communicates the seed 99 to the end of the cannula 128 such that a portion of the seed 99 extends approximately one half its length from an end thereof. Suture material 101 is predisposed over the cannula 128, and a suture clamp 130 applies precise pressure to the suture material 101 around the cannula 128. A suture gripper 132 securely grips an end of the suture material 101. The suture gripper 132 is coupled to a precision linear slide 134 for linear motion. Once a seed 99 is positioned at the end of the cannula 128, the slide 134 advances suture gripper 132 away from suture clamp 130. This motion draws the suture material 101 snugly around the portion of the seed 99 protruding from the end of the cannula 128, and the seed 99 is then drawn from the cannula 128 upon further linear movement of the suture gripper 132. A precise, predetermined length of suture material 101, with the seed placed therein, is then drawn from the cannula 128, and seed pusher portion 124 cycles again to introduce another seed 99 to the end of the cannuila 128. This is repeated until apparatus 100 has introduced a predetermined number of seeds 99 into the suture material 101, with precise spacing. A strand of suture material 101, now loaded with seeds 99, is then removed from apparatus 100, inserted into a resin carrier (not shown) and then into a metal storage and shielding capsule (not shown). Within the capsule, the suture material 101 may be heat treated if necessary to stiffen the suture material 101 to thereby secure the location of the seeds 99. FIG. 15a, similar to FIG. 15, illustrates operation of the apparatus using spherical seeds 99a.

Figure 18:
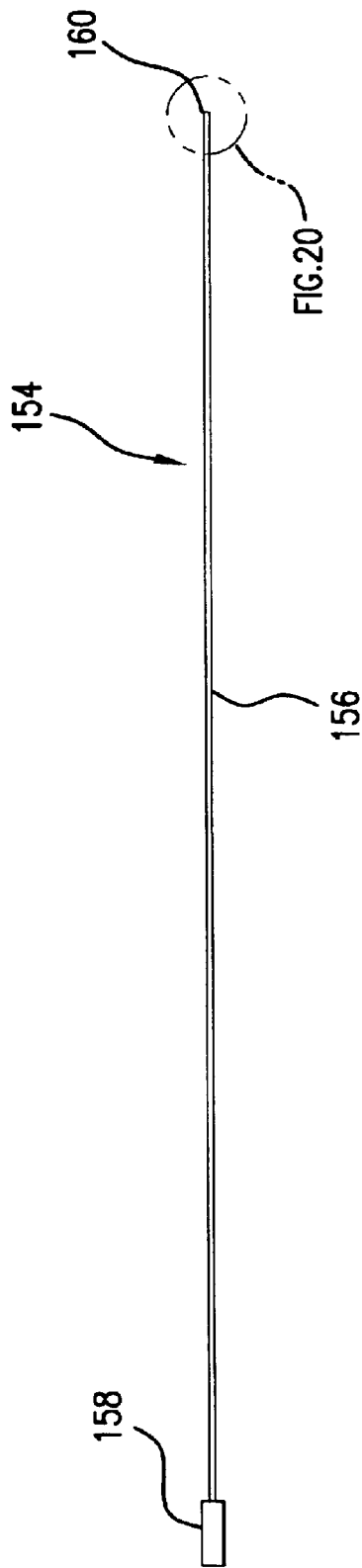
FIG. 18 is a front elevation of a seed pusher for use in the apparatus shown in FIG. 10.
Figure 20:
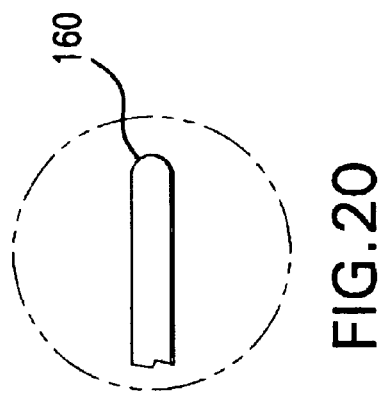
FIG. 20 is an enlarged view of an end portion of the seed pusher illustrated in FIG. 18.
Figure 19:
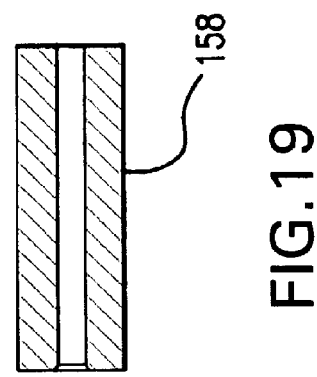
FIG. 19 is a partial cross-section of the seed pusher illustrated in FIG. 18.
Figure 21:
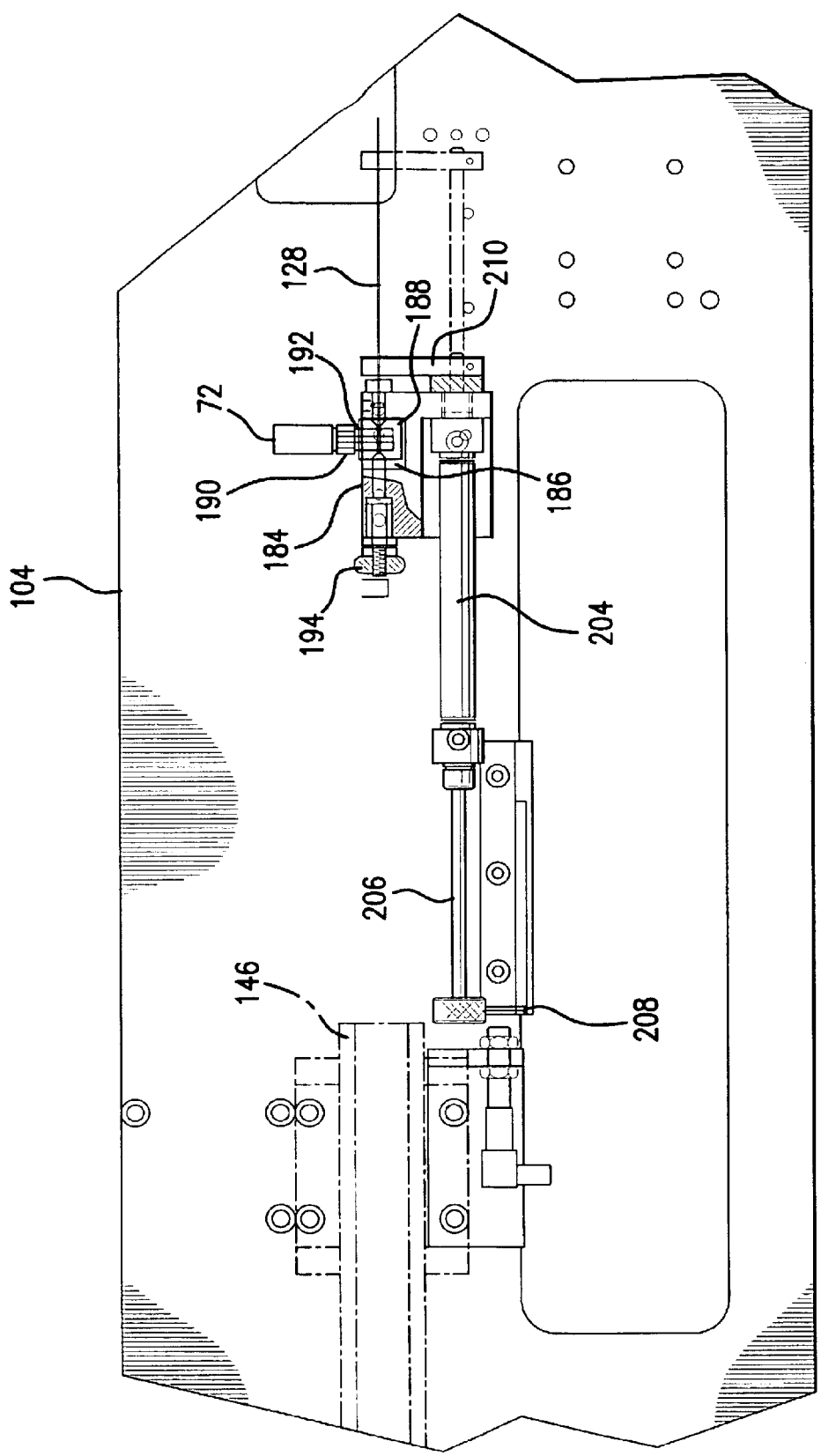
FIG. 21 is a partial front elevation of the apparatus illustrated in FIG. 10.
Figure 22:
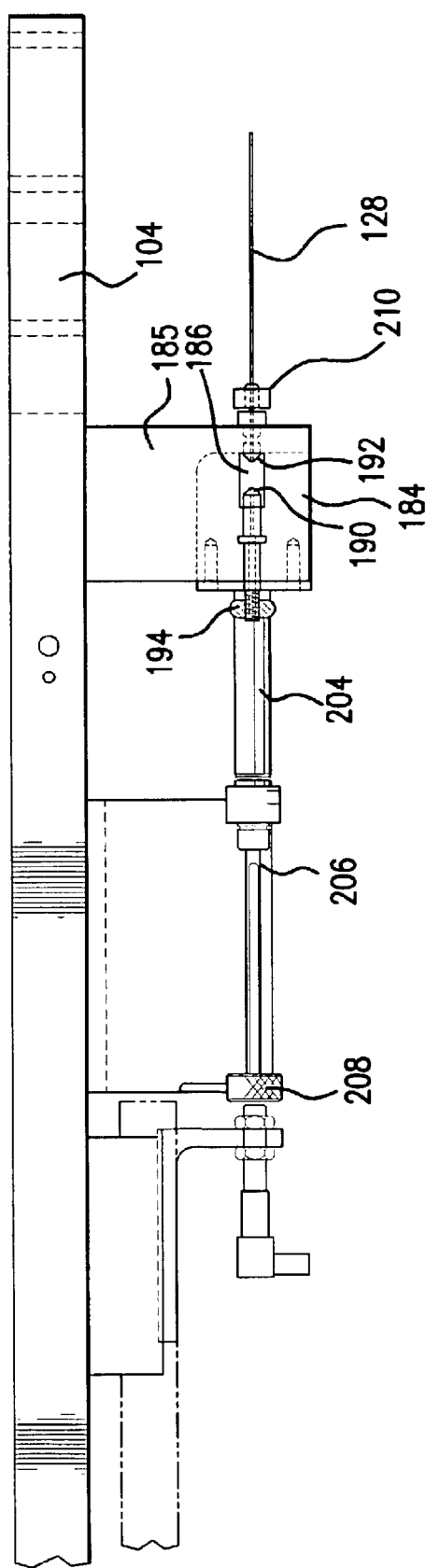
FIG. 22 is a plan view of the portion of the apparatus illustrated in FIG. 21.
Figure 26:
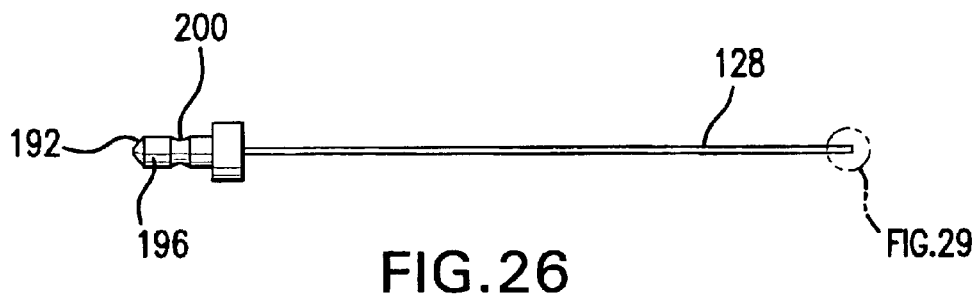
FIG. 26 is a front elevation of a cannula for use in the apparatus illustrated in FIG. 10.
Figure 27:
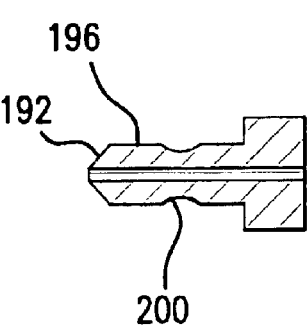
FIG. 27 is a partial cross-section view of the cannula illustrated in FIG. 26.
Figure 28:
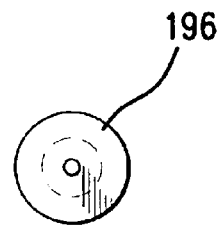
FIG. 28 is a left side view of the cannula illustrated in FIG. 26.
Figure 29:
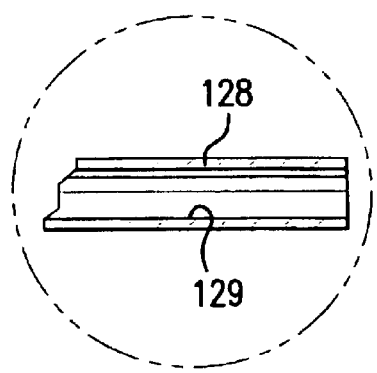
FIG. 29 is an enlarged view of an end portion of the cannula illustrated in FIG. 26.
Figure 30:
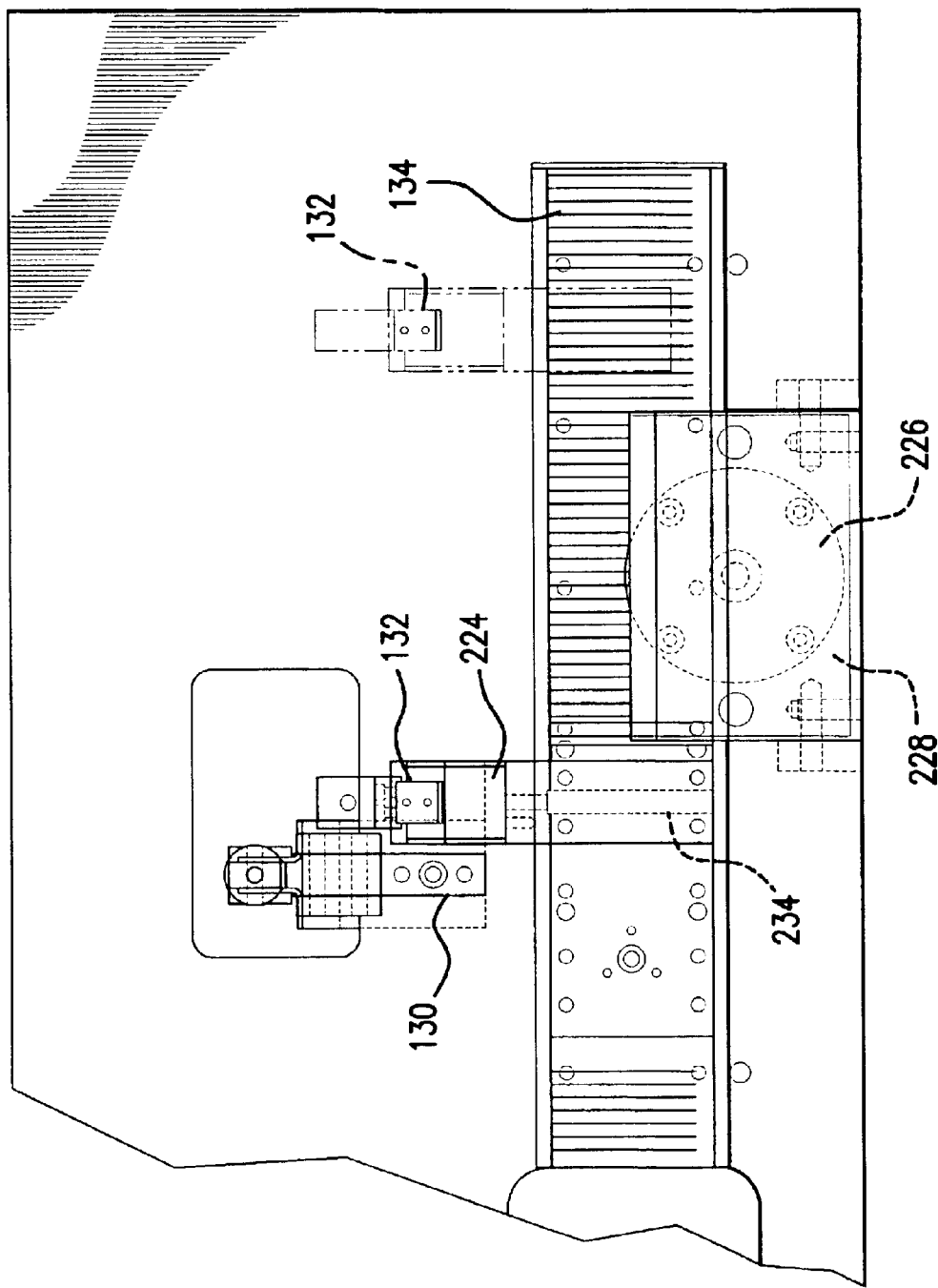
FIG. 30 is a partial front elevation view of a portion of the apparatus illustrated in FIG. 10.
Figure 31:
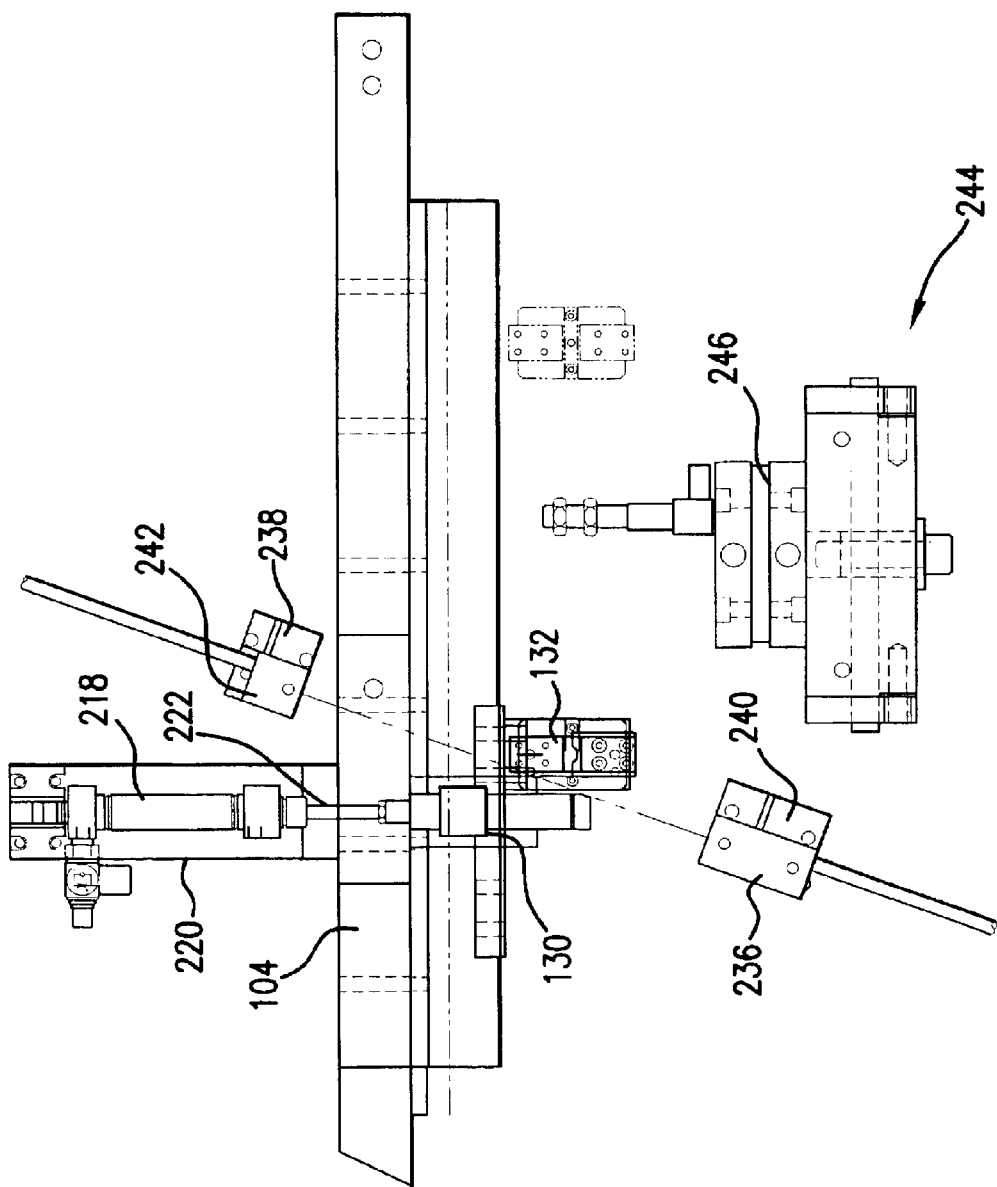
FIG. 31 is a partial plan view of the portion of the apparatus shown in FIG. 30.
Figure 37:
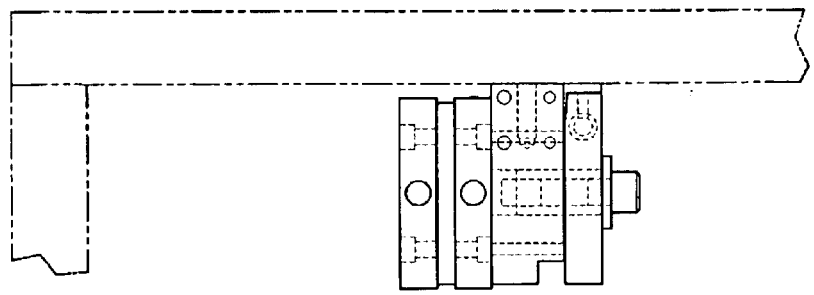
FIG. 37 is a partial right side elevation of the portion of the apparatus illustrated in FIG. 30.
Figure 36:
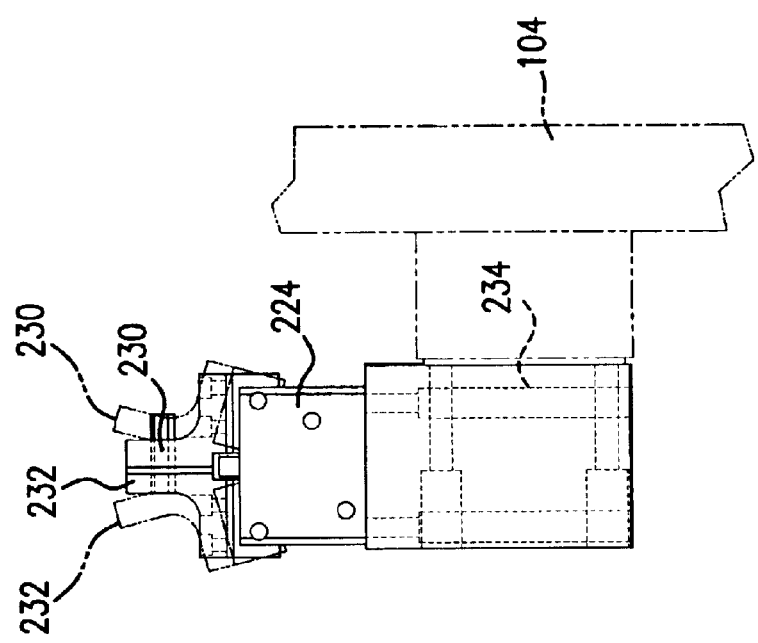
FIG. 36 is a right side elevation of the portion of the apparatus illustrated in FIG. 35.
Figure 35:
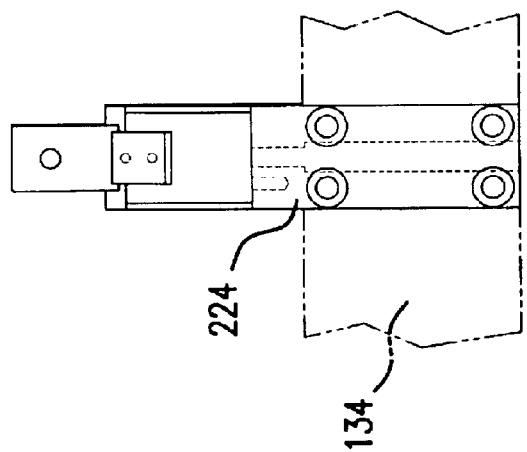
FIG. 35 is a partial front elevation of the apparatus illustrated in FIG. 10.

With reference again to FIGS. 10–13 the seed pusher portion 124 includes a servo motor 136 coupled by a gearbox reducer 138 to a drive arm 140. The servo motor 136 and gearbox reducer 138 are secured to the wall 104 by a motor mounting plate 142. The drive arm 140 is preferably journally supported through the motor mounting plate 142. The drive arm 140 is coupled by a first cam 144 to a first linear slide 146 and by a second cam 145 to a second linear slide 148. The first linear slide 146 slides in a support member 150 and has a pusher block 152 secured to an end thereof Secured to the pusher block 152 is a seed pusher 154. Referring briefly to FIGS. 18–20, seed pusher 154 includes an elongate rod 156 fitted with a mounting block 158 at a first end and has a polished radius second end 160. The rod 156 has a diameter of slightly less than the diameter of the seeds, and preferably about 0.029 inch, and may be preferably made from 12 gauge stainless steel music wire.

The second linear slide 148 slides in a support member 162, and has fitted on an end thereof a rod support 164. Rod support 164 extends from second linear slide 148 and is formed with an aperture, and rod 156 is disposed through the aperture. The servo motor 136 rotates drive arm 140 through an included angle of approximately 62 degrees, and first linear slide 146 and second linear slide 148 are translated in response thereto. Preferably first linear slide 146 translates through a stroke of about 6 inches while the second linear slide 148 has a stroke of approximately 3 inches. As will be appreciated, translation of the first linear slide 146 advances the seed pusher 154. Simultaneously therewith, the rod support 164 is translated, approximately half the total translation of seed pusher 154, for supporting the rod 156 during operation of seed pusher portion 124.

With continued reference to FIGS. 10–13, a pair of brackets 166 are secured to the wall 104 that support a pair of proximity probes 168 that are arranged to detect a second end of the first linear slide 146 in its retracted most position. A bracket 170 is also secured to the wall 104 and supports a proximity probe 172 that is arranged to detect an extended most position of second linear slide 148.

The pusher block 152 includes an end wall 174. The end wall 174 is mounted on a pivot 176 supported on a lower support member 178. Rod block 158 is secured to the end wall 174, and the end wall 174 is held in place by a magnet. If a force on seed pusher 154 exceeds a predetermined value, such as would indicate a jamming of apparatus 100, the magnet force holding the end wall 174 in place is overcome and the end wall 174 pivots open. A proximity sensor 180 is mounted to a flange portion 182 of the pusher block 152 and detects the opening of the end wall 174 signaling the overload condition and permitting the shutting down of the apparatus 100 prior to damaging the seed pusher 152 or another portion of the apparatus 100. The force exerted by the magnet may be selected to provide varying levels of overload protection.

Figure 12:
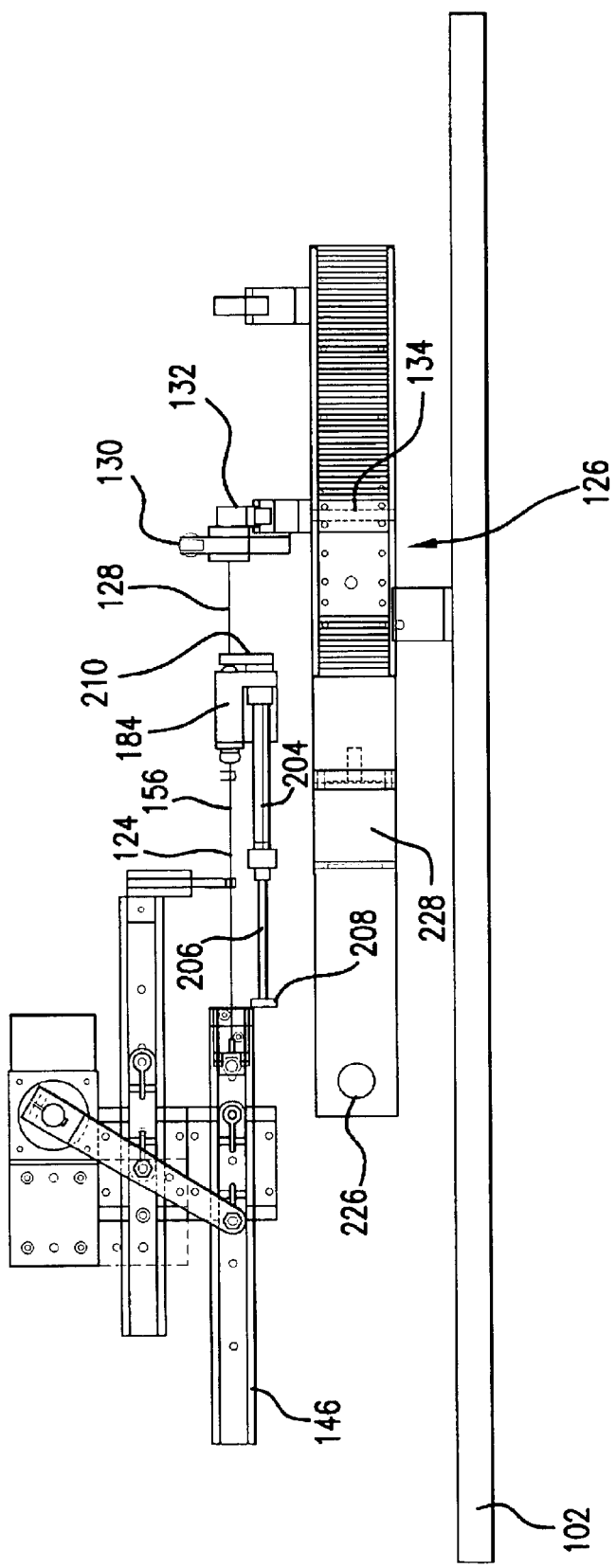
FIG. 12 is a front elevation view of an apparatus similar to that shown in FIG. 10.
Figure 13:
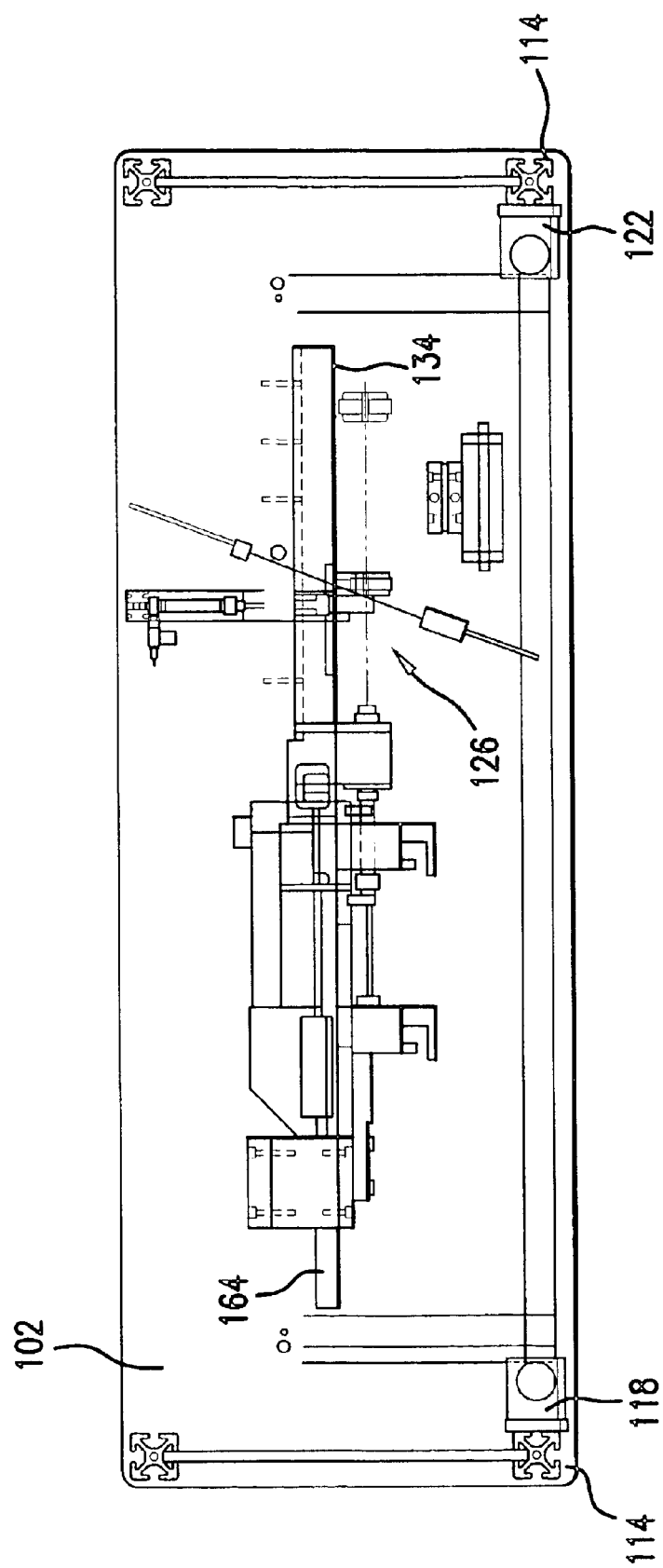
FIG. 13 is a plan view of the apparatus show in FIG. 12.

As is best seen in FIG. 12, the end 160 of the rod 156 is received within a magazine loader 184 of the apparatus 100 and to which the cannula 128 is secured. With the first linear slide 146 fully retracted, the end 160 is retracted from the cannula 128 and a magazine secured to the magazine loader 184. As the first linear slide 146 is extended, the end 160 engages a seed 99 from the magazine and upon further extension of linear slide 146 communicates the seed 99 into the cannula 128 and along its length for loading into the suture material as described above.

With reference still to FIGS. 10–13, and also now to FIGS. 21–25, the magazine loader 184 is secured to a bracket 185 extending from the wall 104. The magazine loader 184 is formed with an square aperture 186 into which a magazine retainer 188 is disposed. The magazine is secured to the magazine retainer 188. The magazine retainer 188 is secured between a pair of tapers 190 and 192, respectively formed in magazine lock 194 and cannula hub 196. Magazine lock is spring biased to bear against magazine retainer 188, and thereby secures and accurately positions the magazine retainer 188, and hence the magazine, with respect to cannula hub 196, and hence cannula 128. Cannula 128, including cannula hub 196, is held in magazine retainer 196 by the engagement of cannula lock 198 with a groove 200 formed in cannula hub 196. Cannula 128 and cannula hub 196 are shown in more detail in FIGS. 26–29.

The extension of seed pusher 124 into magazine retainer 188, engages the rod end 160 with a seed 99 held within the magazine and communicates the seed into cannula 128. The tapers 190 and 192 ensure precise alignment of the rod 156, the magazine and particularly a discharge aperture formed therein, and the lengthwise aperture 129 formed within the cannula 128. The tapers further ensure precise linear relationship between the apparatus 100 and the end 202 of the cannula 128. This feature ensures that after cannula 128 has been removed from the magazine retainer 188 in order to place suture material 101 thereon, it is once again quickly and easily realigned with the apparatus 100.

With continued reference to FIGS. 21–25, also secured to magazine retainer 188 is an air cylinder 204 having a cylinder rod 206. A first end of the cylinder rod 206 is fitted with a knob 208 and a second end is fitted with a slider 210 that is formed with an aperture. Cannula 128 is received through the aperture, and the slider 210 engages suture material disposed on the cannula 128. As the first linear slide 146 is advanced, it engages the knob 208 thereby advancing the rod 206. The slider 210 engages the suture material disposed on the cannula 128 and bunches it toward and end thereof. This feature ensures proper feeding of suture material during seed loading. Air cylinder 204 is then operable to return the rod 206 to its retracted position with the return of the linear slide 146 to its retracted position.

With reference now to FIG. 12 and FIGS. 30–37, suture clamp 130 is disposed adjacent the end of cannula 128 and includes a lower clamping member 208 and an upper clamping member 210, each of which are formed with arcuate reliefs 212 and 214, respectively. Suture clamp 130 is arranged to clamp around the cannula 128 and to engage the suture material disposed thereon to ensure a desired tension in the suture material as it is drawn off of the cannula 128. The lower clamping member 208 and the upper clamping member 210 are each made from steel that is flash plated with chrome to resist wear. The lower clamping member 208 is secured by a bracket 216 to the wall 104. The upper clamping member 210 is pivotably secured to the lower clamping member 208 and is further coupled to an air cylinder 218. The air cylinder 218 is secured to a bracket 220 on an opposite side of the wall 104, and has a rod 222 that extends through an aperture in the wall 104 and that couples to the upper clamping member 210.

The suture gripper 132 is secured to a gripper mount 224 that in turn is secured to the linear slide 134. The linear slide 134 is preferably a precision linear slide that is coupled to a servo motor 226 via a reduction gearbox 228. The suture gripper 132 includes a first gripper member 230 and a second gripper member 232, which are preferably made of stainless steel, coupled via a toggle mechanism to an air cylinder 234 (shown in phantom). Actuation of the air cylinder 234 draws together the first and second gripper members 230 and 232, to securely grip the suture material. The opening range of the first and second gripper members 230 and 232 is preferably limited to prevent catching an operator's fingers therein.

The linear slide 134 acts to extend suture gripper 132 upon detection of a seed 99 at the end of cannula 128. A first standard 236 and a second standard 238 respectively support a laser sending device 240 and a laser detection device 242 that is positioned to observe the end of the cannula 128. In this manner, the presence of a seed at the end of the cannula 128 is detected prior to extending the suture gripper 132 from suture clamp 130.

A finishing jig 244 is secured to the base 102 that includes a channel 246 into which a resin retainer is held. Suture material 101 having seeds 99 disposed therein is positioned within the resin retainer, and then into the storage capsule. The resin retainer also advantageously permits visual inspection of the strand to ensure that the correct number of seeds 99 has been disposed within the suture material 101 with the correct spacing.

As should be further appreciated suitable pneumatic couplings, solenoid actuated valves, electrical actuators and programmable controllers are operatively coupled to apparatus 10 and apparatus 100 for operation in accordance with the foregoing description.

What is claimed is:

1. An automated method of loading a delivery system for brachytherapy seeds which comprises the steps of:
    a) securing the delivery system to be loaded;
    b) communicating seeds from a supply of seeds into the delivery system; and
    c) repeating step b) to load a plurality of seeds, wherein the delivery system for brachytherapy seeds includes a portion of suture material.

2. The method of claim 1 further comprising:
    a) providing the supply of seeds as a magazine containing a plurality of seeds;
    b) disposing the suture material over a cannula;
    c) tensioning the suture material about an output end of the cannula;
    d) communicating a seed from the magazine to the output end of the cannula;
    e) drawing a portion of the suture material from the cannula thereby engaging the seed within the portion of suture material; and
    f) repeating steps (d) and (e) for a plurality of seeds.

3. The method of claim 2, wherein the step of tensioning comprises clamping the suture material about the cannula and gripping a free end of the suture material at the output end of the cannula.

4. The method of claim 2, wherein the step of communicating includes positioning the seed at the output end of the cannula such that a portion of the seed extends beyond the output end of the cannula.

5. The method of claim 2, wherein the step of communicating includes engaging a seed from within the magazine, introducing the seed into the cannula at an input end of the cannula and conducting the seed along the cannula to the output end.

6. The method of claim 2, wherein the step of communicating includes providing a rod member coupled to a reciprocating drive.

7. The method of claim 2, wherein the step of drawing includes gripping a free end of the suture material adjacent the output end of the cannula and displacing the free end relative to the output end, preferably, drawing a predetermined length of suture material.

8. The method of claim 2, wherein the step of drawing includes providing a linear slide mechanism coupled to a gripper, the gripper being arranged to grip a free end of the suture material adjacent the output end of the cannula.

9. The method of claim 2, wherein the step of providing a magazine includes securing the magazine within a magazine receiver and aligning the cannula to the magazine receiver.

10. The method of claim 2, further comprising before step (e) the step of detecting a presence of a seed at the output end of the cannula.

11. An apparatus for loading a delivery system for brachytherapy seeds comprising:
    a) means for retaining a delivery system to be loaded with seeds; and
    b) means for communicating individual seeds from a supply of seeds to said delivery system, wherein the delivery system comprises a seed magazine, and the apparatus further comprises:
    a base;
    a hopper supported above the base, the hopper being sized to retain a plurality of seeds therein;
    a seed conveyor, comprising a vibratory feeder, supported above the base and coupled to the hopper, the seed conveyor having a feed path, the feed path being sized to separate and align individual ones of the plurality of seeds;
    a tooling nest supported above the base, the tooling nest formed to include a magazine receiver and a seed staging area, the seed staging area being coupled to the feed path and the magazine receiver being sized to receive the seed magazine and to align an opening of the seed magazine with the staging area;
    a pusher member slidably supported above the base and adjacent to the staging area;
    a reciprocating drive coupled to the pusher member to impart reciprocating driving motion to the pusher member; and
    wherein, during operation of the apparatus, a seed is communicated by the seed conveyor along the seed path from the hopper to the staging area and aligned within the staging area, responsive to the reciprocating driving motion, the pusher member engages the seed and introduces the seed through the opening of the seed magazine and into the seed magazine.

12. The apparatus as claimed in claim 11 further comprising an air jet supported above the base, the air jet being aligned with a portion of the feed path adjacent the staging area and being coupled to a source of compressed air such that a jet of air is directed along the portion of the feed path for urging a seed being communicated along the feed path toward the staging area and, preferably, wherein the air jet further comprises a valve for selectively interrupting the jet of air, the operation of the valve being timed to the reciprocating driving motion of the pusher member.

13. The apparatus of claim 11, the tooling nest being mounted on an arm, the arm being moveably supported above the base and pivotable between a first position and a second position, wherein in the first position the staging area is aligned with the feed path and in the second position the magazine receiver is accessible to an operator for introducing a seed magazine therein.

14. The apparatus of claim 11, wherein the reciprocating drive comprises a first actuator having a first stroke and a second actuator having a second stroke different than the first stroke, the first stroke being set to conduct the pusher member to a first position immediately adjacent the opening in the seed magazine and the second stroke being set to conduct the pusher member to a second position wherein an end of the pusher member extends through the opening in the seed magazine and into the seed magazine.

15. The apparatus of claim 11, further comprising a swing arm supported above the base and adjacent the staging area, the swing arm being positioned to engage a seed positioned in the staging area and to guide said seed into the magazine in cooperation with operation of the pusher member.

16. The apparatus of claim 11, further comprising a finger member, the finger member being pivotably supported above the base and having a notch portion and an angle portion, the finger member being biased in a first position wherein the notch portion engages a lower portion of the seed magazine and occludes an opening of the seed magazine, and the angle portion is disposed in opposing relationship to said opening and adjacent the seed staging area, and the finger member being moveable to a second position by engagement of the pusher member with the angle portion for introduction of seeds into said magazine through said opening.

17. The apparatus of claim 11, wherein the seed conveyor is sized to align a seed substantially along a longitudinal axis of said seed.

18. The apparatus of claim 11 wherein the delivery system comprises a portion of suture material.

19. The apparatus of claim 18 which includes:
a cannula, the portion of suture material being disposed on the cannula;
means for communicating seeds from a magazine containing a plurality of seeds into the cannula and to an output end of the cannula; means for tensioning the suture material about the output end of the cannula; means for drawing a portion of suture material, under tension, from the cannula; and
wherein, a seed disposed at the output end of the cannula is engaged by the portion of suture material and drawn from the cannula and into the suture material.

20. The apparatus of claim 19 wherein the means for communicating is further operable to sequentially communicate seeds from the magazine to the output end of the cannula.

21. The apparatus of claim 19, herein the means for communicating seeds comprises means for receiving the magazine, the means for receiving the magazine being further operable to align an input end of the cannula to the magazine.

22. The apparatus of claim 19, wherein the means for tensioning comprises means for engaging a portion of material disposed on the cannula and means for gripping an end portion of the suture material.

23. The apparatus of claim 19, wherein the means for drawing comprises means for displacing the means for gripping linearly relative to the output end of the cannula.

24. The apparatus of claim 19, further comprising means for detecting a seed at the output end of the cannula and wherein the means for drawing is responsive to the means for detecting for drawing the portion of suture material.

25. The apparatus of claim 18 which includes:
a base;
a seed pusher portion and a suture material feeder portion, each of the seed pusher portion and the suture material feeder portion being supported from the base;
the seed pusher portion comprising:
a magazine receiver adapted to receive a magazine containing a plurality of seeds;
a cannula extending from the magazine receiver, the cannula having an input end and
an output end, the input end being aligned to the magazine receiver;
a rod member slidably mounted from the base, the rod member being sized to be received within the cannula;
a reciprocating drive coupled to the rod member, the reciprocating drive imparting a reciprocating linear motion to the rod member such that an end of the rod member is advanced through the magazine receiver and into the cannula, the end thereby being extended into the cannula toward the output end;
the suture material drive comprising:
a first suture clamp disposed about the output end of the cannula and adapted to engage a portion of suture material disposed on the cannula;
a second suture clamp adapted to clamp an end of the portion of suture material,
a linear slide coupled to the base and coupled to the second suture clamp, the linear slide arranged for linear displacement relative to the output end; and
wherein, in operation of the apparatus, the rod member is advanced by the reciprocating drive into the magazine receiver and the end of the rod member engages a seed within a seed magazine disposed within the magazine receiver and communicates the seed from the input end of the cannula to the output end of the cannula, the second suture clamp is displaced from the output end of the cannula drawing the portion of suture material taught between the first clamp and the second clamp such that the seed is engaged by the suture material and drawn from the output end of the cannula and into the suture material.

26. The apparatus of claim 25, further comprising a laser detector positioned to detect a presence of a seed at the output end of the cannula, and wherein the linear slide is responsive to a signal from the laser detector indicating the presence of the seed to displace the second clamp from the output end of the cannula.

27. The apparatus of claim 25, wherein the linear slide incrementally displaces, preferably in predetermined incremental steps, the second suture clamp from the output end of the cannula.

28. The apparatus of claim 25, wherein the end of the rod member comprises a polished radial surface.

29. The apparatus of claim 25, wherein the input end of the cannula is formed with a tapered projection and the magazine receiver is formed with a tapered recess corresponding to the tapered projection, and wherein the tapered projection is received within the tapered recess to align the cannula to the magazine receiver.

30. The apparatus of claim 25, wherein with the rod member extending into the cannula, a portion of a seed extends outwardly from the output end of the cannula.

31. The apparatus of claim 25, further comprising a rod support coupled to the reciprocating drive, the rod support arranged to support the rod member as the rod member is advanced into the cannula.

32. The apparatus of claim 25, further comprising a slider, the slider formed with an aperture and the cannula received through the aperture and the slider coupled to the reciprocating drive, and wherein the slider is advanced along the cannula as the rod member is advanced within the cannula, the slider engaging suture material disposed on the cannula to bunch the material toward the first suture clamp.

33. The apparatus of claim 25, wherein the seed pusher further comprises a means for detecting overload force on the rod member, said means comprising:

an end wall secured to the opposite end of the rod member to that which extends into the cannula, the end wall being secured to a lower support member via a pivot and held in a closed position by a magnet; and a proximity sensor arranged to detect and signal the position of the end wall;

wherein, in operation of the apparatus, an overload force on the rod member causes the magnetic force holding the end wall in the closed position to be overcome and the end wall to pivot open, the proximity sensor detects the opening of the end wall signaling the overload force and causing the apparatus to shut down.

\* \* \* \* \*

UNITED STATES PATENT AND TRADEMARK OFFICE
CERTIFICATE OF CORRECTION

PATENT NO. : 6,730,013 B1
DATED : May 4, 2004
INVENTOR(S) : Charles E. Shanks, John Mueller and Kevin Helle It is certified that error appears in the above-identified patent and that said Letters Patent is hereby corrected as shown below:

Title page,
Item [12], "Shank et al." should be -- Shanks et al. --
Item [75], Inventor, "Kevin Helle's" address of "Barelett" should be -- Bartlett --
Item [86], 371(c)(1),(2), (4) Date:, "January 3, 2002" should be -- April 8, 2003 --

Signed and Sealed this

Twenty-seventh Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,730,013 B1  Page 1 of 1
DATED : May 4, 2004
INVENTOR(S) : Charles E. Shanks et al.

It is certified that error appears in the above-identified patent and that said Letters Patent is hereby corrected as shown below:

<u>Title page,</u>
Item [75], Inventors, "Charles E. Shank, Schaunburg" should be -- Charles E. Shanks, Schamburg --.

Signed and Sealed this

Ninth Day of May, 2006

JON W. DUDAS
*Director of the United States Patent and Trademark Office*